US012029579B2

(12) United States Patent
Tokuno et al.

(10) Patent No.: US 12,029,579 B2
(45) Date of Patent: Jul. 9, 2024

(54) APPARATUS FOR ESTIMATING MENTAL/NEUROLOGICAL DISEASE

(71) Applicants: PST Inc., Kanagawa (JP); The University of Tokyo, Tokyo (JP)

(72) Inventors: Shinichi Tokuno, Tokyo (JP); Shuji Shinohara, Tokyo (JP); Mitsuteru Nakamura, Tokyo (JP); Yasuhiro Omiya, Kanagawa (JP)

(73) Assignees: PST INC., Kanagawa (JP); THE UNIVERSITY OF TOKYO, Tokyo (JP)

( * ) Notice: Subject to any disclaimer, the term of this patent is extended or adjusted under 35 U.S.C. 154(b) by 655 days.

(21) Appl. No.: 17/258,948

(22) PCT Filed: Jul. 11, 2019

(86) PCT No.: PCT/JP2019/027587
§ 371 (c)(1),
(2) Date: Jan. 8, 2021

(87) PCT Pub. No.: WO2020/013296
PCT Pub. Date: Jan. 16, 2020

(65) Prior Publication Data
US 2021/0121125 A1    Apr. 29, 2021

(30) Foreign Application Priority Data
Jul. 13, 2018   (JP) .................. 2018-133333

(51) Int. Cl.
*G16H 50/20*       (2018.01)
*A61B 5/00*        (2006.01)
(Continued)

(52) U.S. Cl.
CPC ............ *A61B 5/4803* (2013.01); *A61B 5/165* (2013.01); *A61B 5/4082* (2013.01);
(Continued)

(58) Field of Classification Search
CPC ........ G10L 17/26; G16H 50/70; G16H 10/40; G16H 50/20
See application file for complete search history.

(56) References Cited

U.S. PATENT DOCUMENTS 8,738,370 B2    5/2014  Mitsuyoshi et al.
10,293,160 B2 *  5/2019  Errico ................ A61N 1/36025
(Continued)

FOREIGN PATENT DOCUMENTS

EP         2851369 A2 *  3/2015  ........... A61K 31/232
JP         2011-255106       12/2011
(Continued)

OTHER PUBLICATIONS

Higuchi, M. et al., "Classification of Bipolar Disorder, Major Depressive Disorder, and Healthy Stateusing Voice", Asain Journal of Pharmaceutical and Clinical Research, Oct. 2018, vol. 11, No. 15, pp. 89-93, <DOI:http://dx.doi.org/10.22159/ajocr.2018.v11s3.30042>.

(Continued)

*Primary Examiner* — Feng-Tzer Tzeng
(74) *Attorney, Agent, or Firm* — Greenblum & Bernstein, P.L.C.

(57) ABSTRACT

A medical apparatus for estimating a mental/neurological disease with high precision is provided. This medical apparatus includes a computational processing device, a recording device having an estimation program which causes the computational processing device to execute processing recorded therein, a calculation unit configured to calculate a score of a subject, a detection unit configured to detect a disease whose score exceeds a reference range, and an estimation unit configured to estimate a mental/neurological disease.

7 Claims, 17 Drawing Sheets

(51) Int. Cl.
  *A61B 5/16*   (2006.01)
  *G10L 17/26*  (2013.01)
  *G16H 10/40*  (2018.01)
  *G16H 50/70*  (2018.01)

(52) U.S. Cl.
  CPC ......... *A61B 5/4088* (2013.01); *G16H 50/20* (2018.01); *G10L 17/26* (2013.01); *G16H 10/40* (2018.01); *G16H 50/70* (2018.01)

(56) References Cited

U.S. PATENT DOCUMENTS

| | | | |
|---|---|---|---|
| 11,504,038 B2* | 11/2022 | Howard | A61B 5/167 |
| 2003/0078768 A1 | 4/2003 | Silverman et al. | |
| 2013/0166291 A1* | 6/2013 | Lech | G10L 17/26 |
| | | | 704/231 |
| 2015/0318002 A1 | 11/2015 | Karam et al. | |
| 2017/0354363 A1 | 12/2017 | Quatieri et al. | |
| 2018/0158538 A1* | 6/2018 | Moturu | G16H 10/20 |
| 2018/0214061 A1 | 8/2018 | Knoth et al. | |
| 2019/0142323 A1 | 5/2019 | Mitsuyoshi et al. | |
| 2021/0233660 A1* | 7/2021 | Omiya | A61B 5/0022 |

FOREIGN PATENT DOCUMENTS

| | | | | |
|---|---|---|---|---|
| JP | 2017-532082 | | 11/2017 | |
| JP | 6337362 | | 6/2018 | |
| JP | 2018-121749 | | 8/2018 | |
| JP | 6667907 B2 | * | 3/2020 | |
| JP | 2022020829 A | * | 2/2022 | ............ A61H 23/00 |
| KR | 20220009954 A | * | 4/2010 | |
| KR | 102581657 B1 | * | 11/2018 | |
| WO | 2006/132159 | | 12/2006 | |
| WO | 2015/168606 | | 11/2015 | |
| WO | 2017/138376 | | 8/2017 | |

OTHER PUBLICATIONS

"2018 CBEES-BBS Bali, Indonesia Conference Abstract", 2018 3rd International Conference on Pharmacy and Pharmaceutical Science (ICPPS 2018), Apr. 23, 2018, pp. 1-7, 16, 48, [retrieval date Sep. 17, 2019], internet <URL:http://www.icpps.org/ICPPS2018-program.pdf>.

International Search Report issued in International Patent Application No. PCT/JP2019/027587, dated Oct. 1, 2019.

* cited by examiner

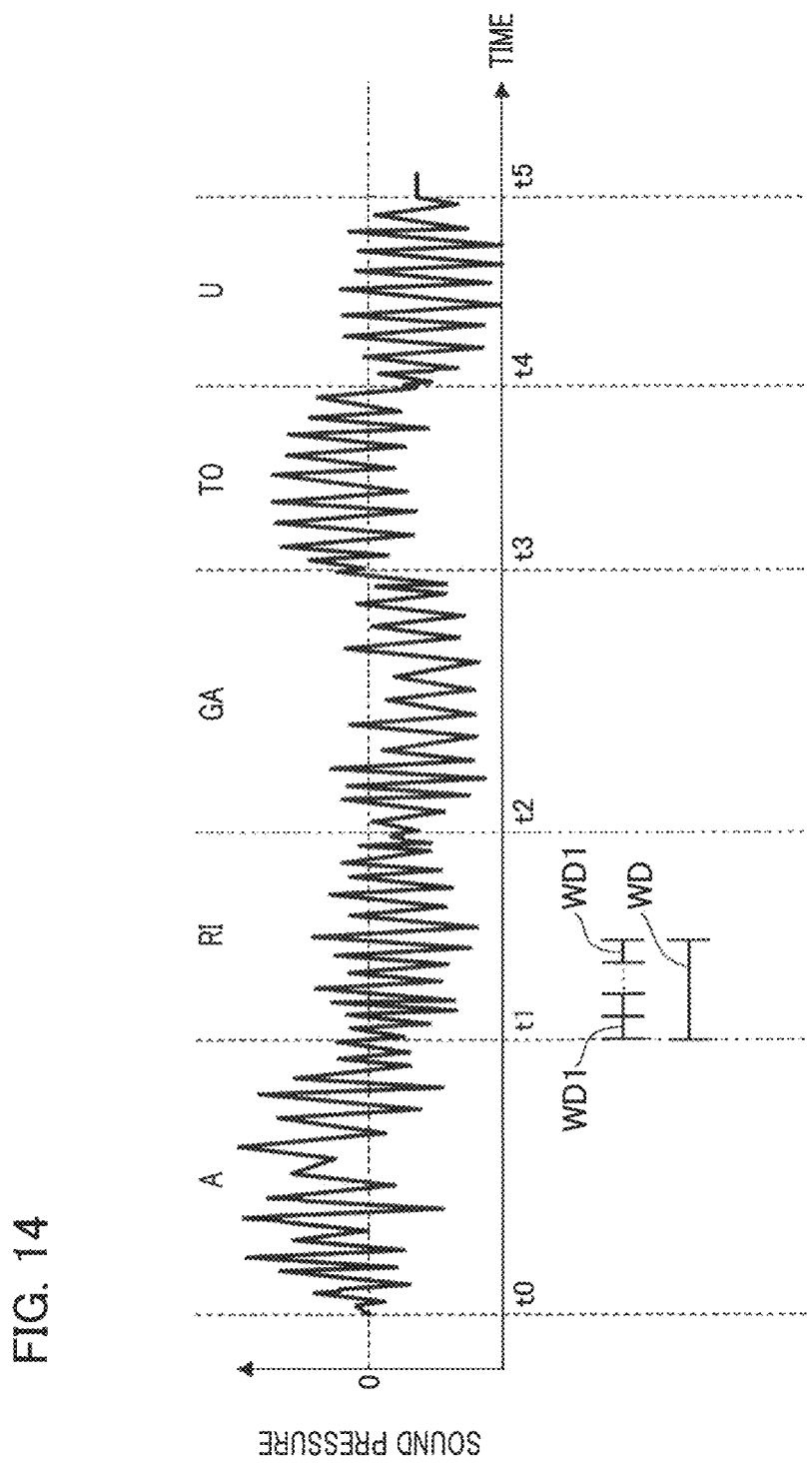

APPARATUS FOR ESTIMATING MENTAL/NEUROLOGICAL DISEASE

CROSS-REFERENCE TO RELATED APPLICATION

Priority is claimed on Japanese Patent Application No. 2018-133333, filed Jul. 13, 2018, the content of which is incorporated herein by reference.

TECHNICAL FIELD

The present invention relates to an apparatus for estimating a mental/neurological disease.

BACKGROUND ART

Technique for estimating emotions by analyzing the speech of subjects are becoming widespread. Patent Literature 1 describes a technique for estimating an emotional state by converting the speech of a subject into a frequency spectrum, obtaining an autocorrelation waveform while performing shifting on a frequency axis, and calculating a pitch frequency from the autocorrelation waveform.

CITATION LIST

Patent Literature

[Patent Literature 1]
PCT International Publication No. WO 2006/132159

SUMMARY OF INVENTION

Technical Problem

However, a range in which estimation can be performed using the above technique is limited to the range in which a person's "emotional" state such as anger, joy, tension, sadness, or depressive symptoms can be estimated and the precision of estimating diseases is not high.

The present invention was made in view of such circumstances, and an object of the present invention is to provide a medical apparatus for estimating a mental/neurological disease with high precision.

In order to achieve the above object, the present invention includes an apparatus which estimates a mental/neurological disease from voice data of speech of a subject including: a computational processing device; a recording device having a diagnosis program which causes the computational processing device to execute processing recorded therein; a calculation unit which calculates a score for the subject by calculating a first acoustic parameter from the voice data acquired from the subject and calculating a feature quantity using a second acoustic parameter previously associated with a disease; a detection unit which sets a reference range on the basis of the feature quantity and detects a disease whose score exceeds the reference range; and an estimation unit which estimates the mental/neurological disease when the detection unit detects one or more diseases.

Advantageous Effects of Invention

According to the present invention, it is possible to provide a medical apparatus for estimating a mental/neurological disease with high precision.

BRIEF DESCRIPTION OF DRAWINGS

FIG. 14 is a diagram for explaining the second acoustic parameter.

DESCRIPTION OF EMBODIMENTS

Embodiment

Embodiments for carrying out the present invention will be described below with reference to the drawings and the like.

Figure 1:
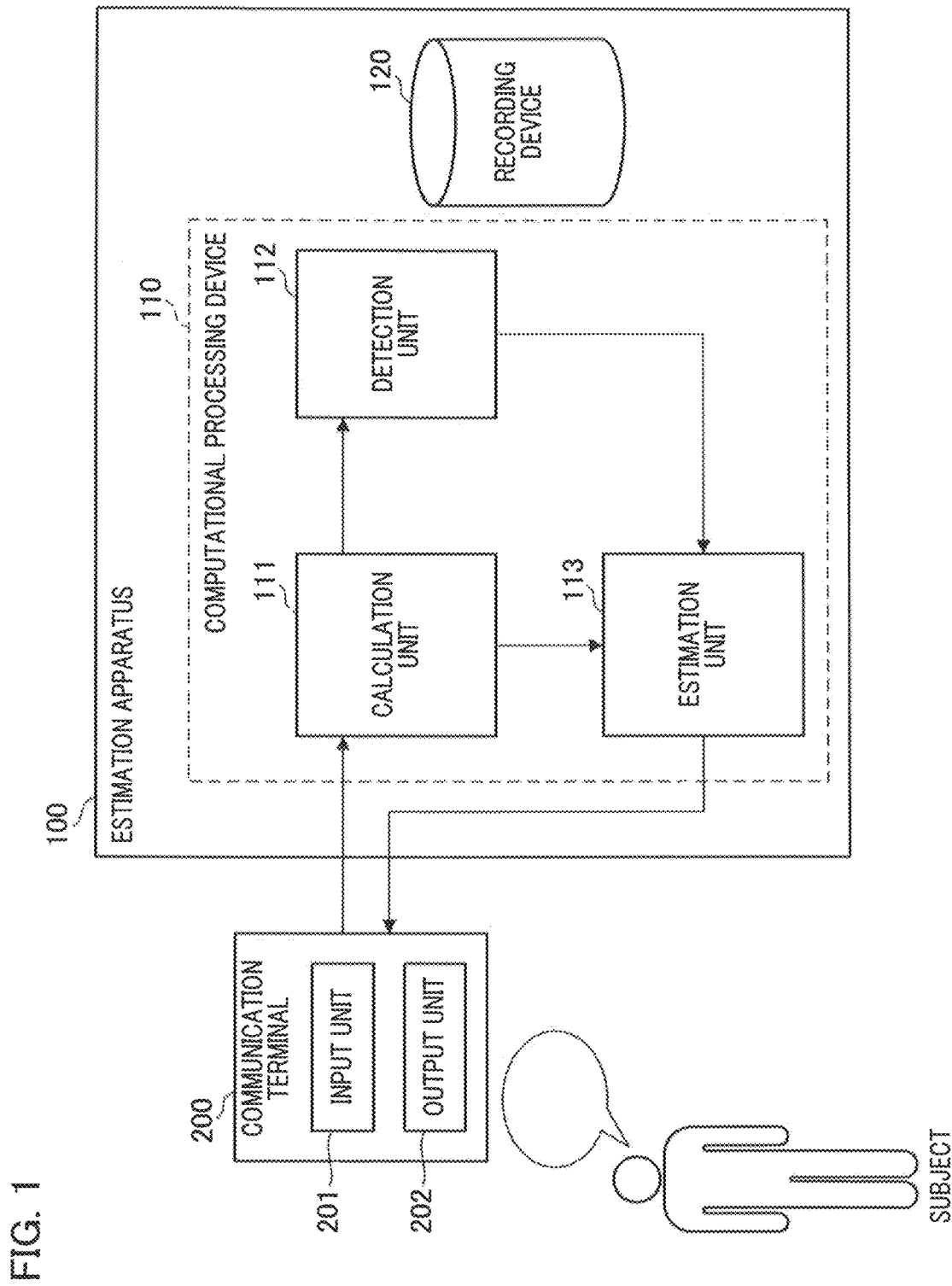
FIG. 1 is a diagram illustrating a configuration of the present invention.

FIG. 1 illustrates a diagram of a configuration of an estimation apparatus 100 of the present invention.

The estimation apparatus 100 in FIG. 1 is a computer which includes a computational processing device 110 (a CPU) and a recording device 120 such as a hard disk having an estimation program which causes the computational processing device 110 to execute an estimation program recorded therein. The computational processing device 110 includes respective functional units including a calculation unit 111, a detection unit 112, and an estimation unit 113. The estimation apparatus 100 is connected to a communication terminal 200 via a wired or wireless connection. The communication terminal 200 includes a voice input unit 201 such as a microphone and a video output unit 202 configured to display estimation results. The calculation unit 111, the detection unit 112, and the estimation unit 113 may be implemented using hardware.

Figure 2:
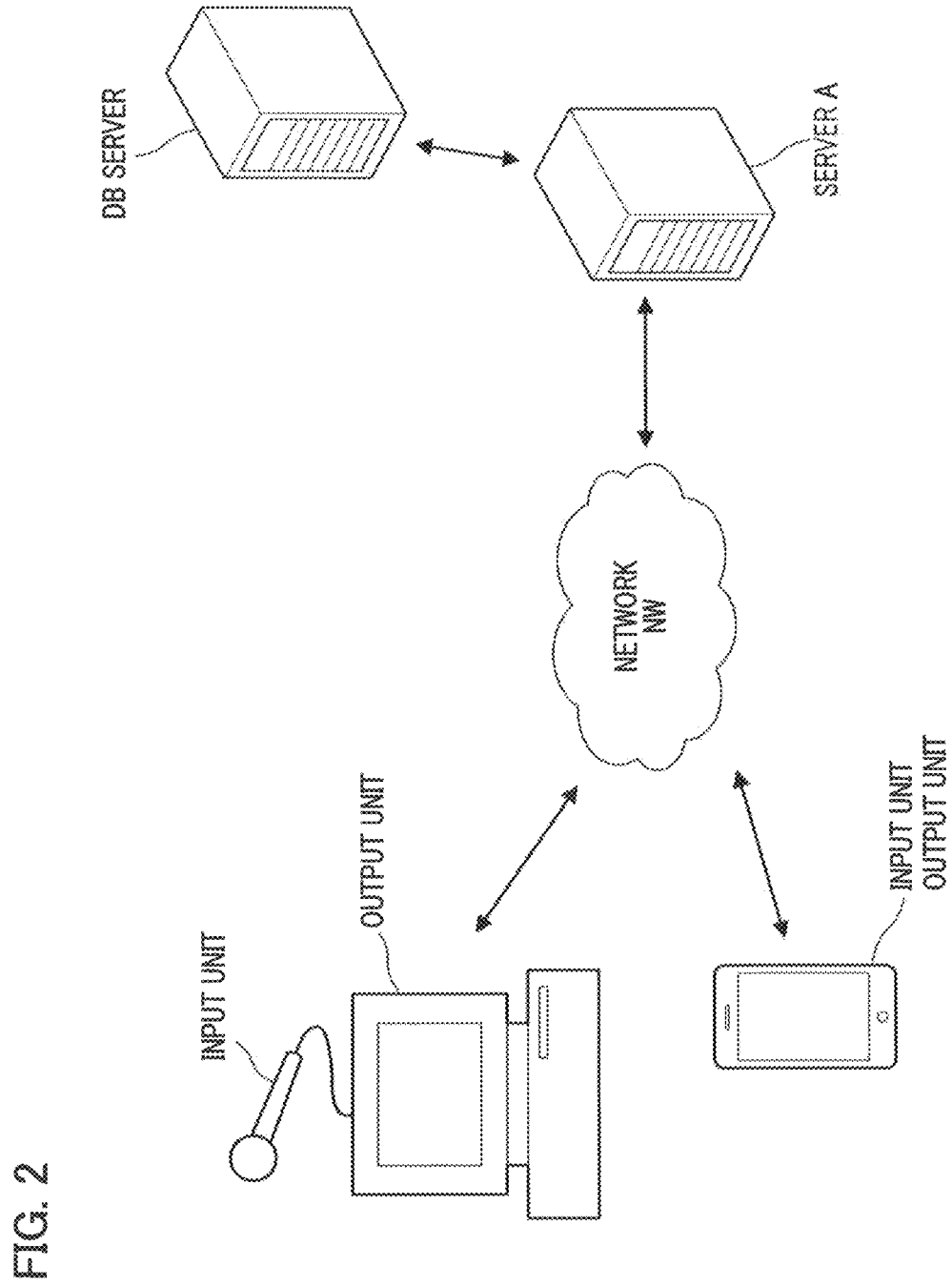
FIG. 2 is a diagram illustrating a configuration of the present invention.

FIG. 2 illustrates an embodiment of the estimation apparatus 100 over a network NW. The estimation apparatus 100 is implemented using a server A which has a computation processing function and a recording function of recording an estimation program and a database (DB) server B having voice data classified by diseases stored therein. The server A may independently perform the processing of the database (DB) server B. In the case of the estimation apparatus 100 illustrated in FIG. 2, the communication terminal 200 is connected to the server A over the network NW and the server A is further connected to the database (DB) server B via a wired or wireless connection.

The estimation apparatus 100 may be implemented using the communication terminal 200. In this case, an estimation program stored in the server A is downloaded over the network NW and recorded in the recording device 120 of the communication terminal 200. When the CPU included in the communication terminal 200 executes an application recorded in the recording device 120 of the communication terminal 200, the communication terminal 200 may function as the calculation unit 111, the detection unit 112, and the estimation unit 113.

The estimation program may be recorded and distributed on an optical disc such as a DVD or a portable recording medium such as a USB memory.

The communication terminal 200 is an apparatus which includes a voice input unit 201 and a video output unit 202. Examples thereof include a laptop computer or a desktop computer which includes a microphone, a smartphone, a tablet-type terminal, and the like. The communication terminal 200 acquires a voice signal of the speech of a subject via a microphone of the communication terminal 200, samples the voice signal at a predetermined sampling frequency (for example, 11 kHz and the like), and generates voice data of a digital signal. The generated voice data is transmitted to the estimation apparatus 100.

The communication terminal 200 displays the estimation result of the estimation apparatus 100 on a display which serves as the video output unit 202. The display is an organic electro-luminescence (EL) display, a liquid crystal display, or the like.

The microphone may be directly connected to the estimation apparatus 100 via a wired or wireless connection. In this case, the estimation apparatus 100 may sample a voice signal from the microphone at a predetermined sampling frequency and acquire voice data of a digital signal.

First Embodiment

Figure 10:
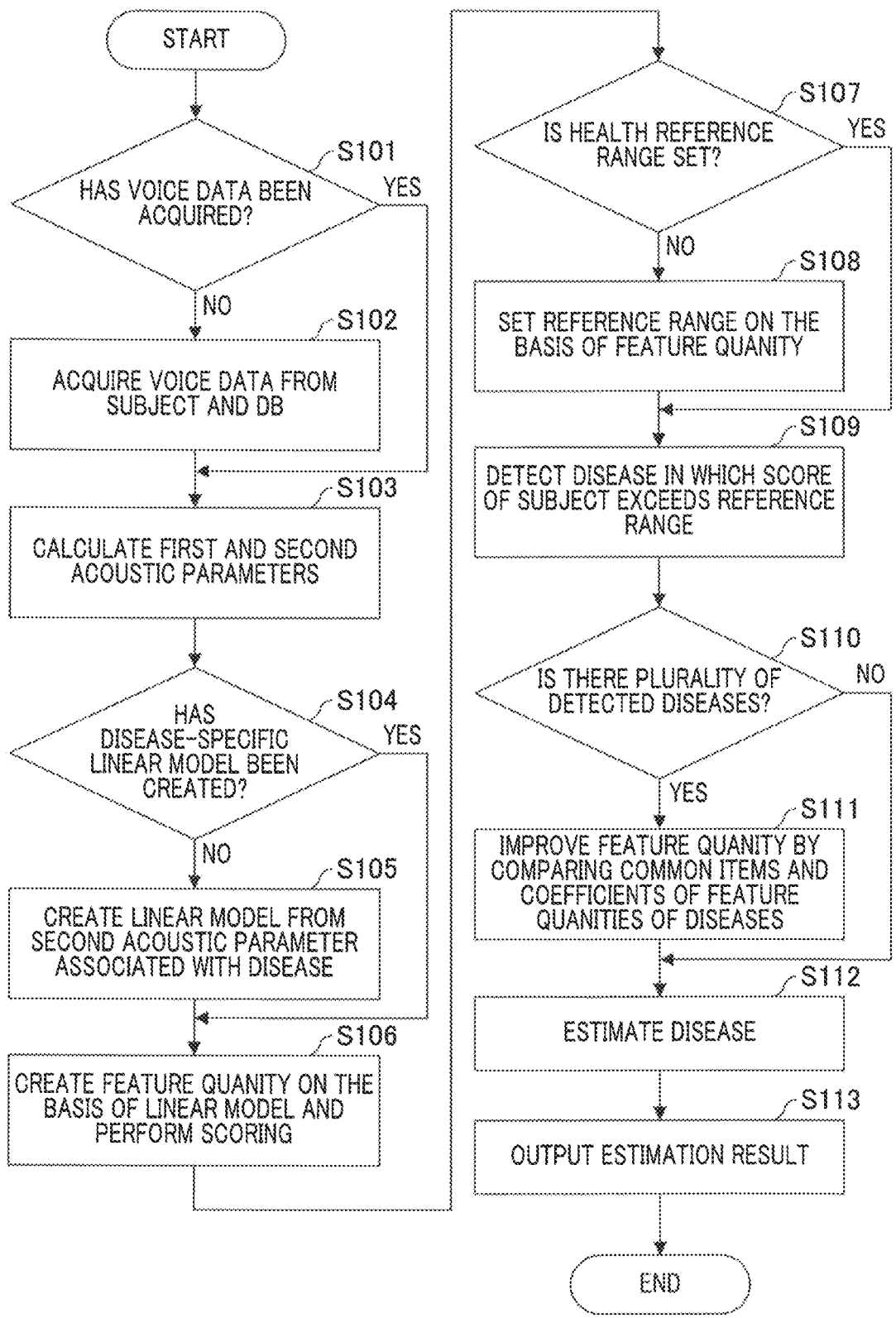
FIG. 10 is a flowchart for describing the present invention.

FIG. 10 illustrates an example of estimation processing in the estimation apparatus 100 illustrated in FIG. 1. The processing illustrated in FIG. 10 is realized using the computational processing device 110 of the estimation apparatus 100 configured to execute the estimation program recorded in the recording device 120 of the estimation apparatus 100. Each function of the calculation unit 111, the detection unit 112, and the estimation unit 113 of the computational processing device 110 will be described with reference to FIG. 10.

(Calculation Unit 111)

When the processing is started, in Step S101, the calculation unit 111 determines whether voice data has been acquired. Two types of data exist as the voice data and one thereof is first voice data acquired from a target subject. The other thereof is second voice data acquired from the database (DB) server B or the like of FIG. 2. The second voice data has been previously associated with respective diseases. The second voice data may be previously recorded in the recording device 120 of the estimation apparatus 100 together with the estimation program.

When it is determined that voice data has already been acquired, the process proceeds to the process of Step S103. When it is determined that voice data has not been acquired yet, in Step S102, voice data is acquired via the communication terminal 200, the database (DB) server B, and the like.

Subsequently, in Step S103, the calculation unit 111 calculates a first acoustic parameter and a second acoustic parameter from the two types of acquired voice data. Acoustic parameters are parameterized features when speech is transmitted and are used as a variable f(n) of a feature quantity which will appear later. The first acoustic parameter is calculated from the first voice data of the subject for whom disease is to be estimated.

The second acoustic parameter is calculated from the second voice data acquired from the database (DB) server B or the like. Since the second voice data is associated with each disease in advance, with regard to the second acoustic parameter which has been calculated, respective diseases are also associated with this acoustic parameter. The second acoustic parameter may be recorded in the recording device 120 of the estimation apparatus 100 in advance together with the estimation program.

A disease group which can be estimated using the estimation apparatus 100, that is, a disease group which is associated with the second voice data in advance, includes Lewy body dementia, Alzheimer's disease, Parkinson's disease, major depression, bipolar disorder, or non-specific depression. Here, the disease group is not limited thereto.

The acoustic parameters include the following:

[Table 1]
1) Sound volume envelope (attack time, decay time, sustain level, and release time)
2) Waveform variation information (Shimmer and Jitter)
3) Zero crossing rate
4) Hurst index
5) Voice onset time (VOT)
6) Statistics of a distribution in speeches associated with a coefficient of a mel frequency cepstrum (a first quartile, a median, a third quartile, a 95% point, an arithmetic mean, a geometric mean, a difference between a third quartile and a median, and the like)
7) Statistics of a distribution in speeches in a rate of change of a frequency spectrum (a first quartile, a median, a third quartile, a 95% point, an arithmetic mean, a geometric mean, a difference between a third quartile and a median, and the like)
8) Statistics of a distribution in speeches associated with a change over time in a coefficient of a mel frequency cepstrum (a first quartile, a median, a third quartile, a 95% point, an arithmetic mean, a geometric mean, a difference between a third quartile and a median, and the like)
9) Statistics of a distribution in speeches associated with a time change of a time change of a coefficient of a mel frequency cepstrum (a first quartile, a median, a third quartile, a 95% point, an arithmetic mean, a geometric mean, a difference between a third quartile and a median, and the like)
10) A square error in a time change within the speech of a frequency spectrum 90% roll-off with respect to quadratic regression approximation
11) An arithmetic error in a time change within the speech of a frequency spectrum center of gravity with respect to quadratic regression approximation. In addition, a pitch rate, the probability of spoken sound, a power of an arbitrary range frequency, a scale, a talk series (the number of mora in a certain time), pause/interval, a sound volume, and the like.

A feature quantity F(a) is created by selecting one or more arbitrary acoustic parameters to be used as the variable f(n) from the above acoustic parameter items and adding a coefficient to the selected arbitrary acoustic parameter. For an arbitrary acoustic parameter used, acoustic parameters having a correlation with a specific disease to be estimated is selected. After a user has selected variables f(n) and coefficients thereof, the estimation program may improve the quality of the feature quantity through machine learning from information or the like stored in the database.

Since there are large differences between numerical values of the acoustic parameters, the respective acoustic parameters may be normalized. Furthermore, when there is a common item in two or more diseases, the feature quantity may be normalized in two or more.

Subsequently, in Step S104, the calculation unit 111 determines whether a disease-specific linear model has been created. When it is determined that a linear model has already been created, the process proceeds to the process of Step S106. When it is determined that a linear model has not been created yet, in Step S105, a linear model is created on the basis of a second acoustic parameter in which each disease is associated with an acoustic parameter.

Subsequently, in Step S106, a feature quantity is created on the basis of the created linear model. The feature quantity can be represented by the following expression F(a). A score of the subject used in the next detection unit 112 is calculated from the first acoustic parameter on the basis of the feature quantity F(a).

$$F(a)=x1\times f(1)+x2\times f(2)-x3\times f(3)+ \ldots +xn\times f(n) \quad \text{[Math. 1]}$$

Here, f(n) is obtained by arbitrarily selecting any one or more second acoustic parameters from the above acoustic parameter items (1) to (11). xn is a disease-specific coefficient. f(n) and xn may be recorded in advance in the recording device 120 of the estimation program. Furthermore, the feature quantity may be improved in the process of machine learning of the estimation program.

The estimation program has a learning function using artificial intelligence and performs estimation processing through this learning function. Neural network type deep learning may be used or reinforcement learning or the like which partially enhances a learning field may be used. In addition, genetic algorithms, cluster analysis, self-organizing maps, ensemble learning, and the like may be used. Of course, other techniques associated with artificial intelligence may be used. In ensemble learning, a classification algorithm may be created through a method in which both boosting and a decision tree are used.

When there is a common item in two or more diseases, the feature quantity may be divided into two or more. For example, the following division is possible.

$$F(ab)=x1\times f(1)+x2\times f(2)+x3\times f(3)+ \ldots +xn\times f(n):$$

Common features of diseases A and B $$F(a)=F(ab)+x'1\times f'(1)+x'2\times f'(2)+ \ldots +x'n\times f'(n):$$

Amount of disease-specific feature of disease A $$F(b)=F(ab)+x''1\times f''(1)+x''2\times f''(2)+ \ldots +x''n\times f''(n): \quad \text{[Math. 2]}$$

Amount of disease-specific feature of disease B

Here, the details of the acoustic parameter will be described.

(1. Sound Volume Envelope)

Figure 3:
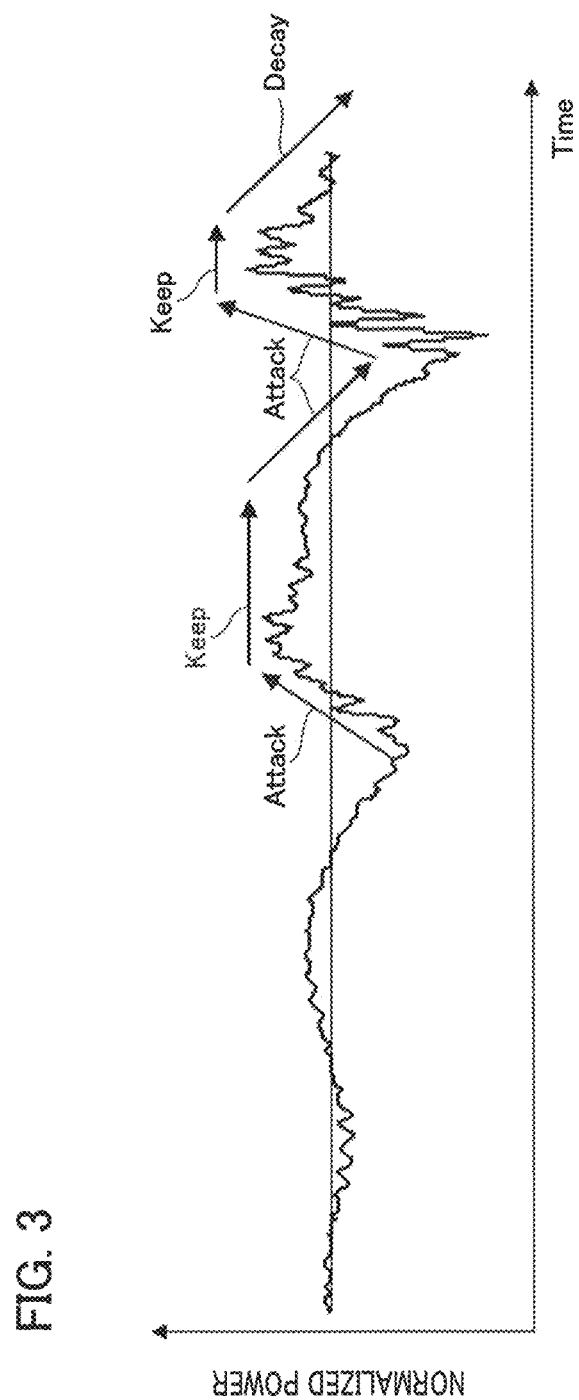
FIG. 3 is a diagram for explaining a second acoustic parameter.

FIG. 3 is an explanatory diagram associated with a sound volume envelope. A horizontal axis represents a time t and a vertical axis represents a normalized power spectral density.

The sound volume envelope includes an attack time, a decay time, a sustain level, and a release time. The attack time ("Attack") is a time from a time at which sound starts to a time at which the sound has reached a maximum sound volume. The decay time ("Decay") is a damping time from a time at which sound is emitted to a time at which the sound has settled at a certain sound volume (a sustain level). The release time is a disappearance time from a time at which sound is emitted to a time at which the sound fully disappears.

(2. Wave Information Regarding Waveform)

Figure 4:
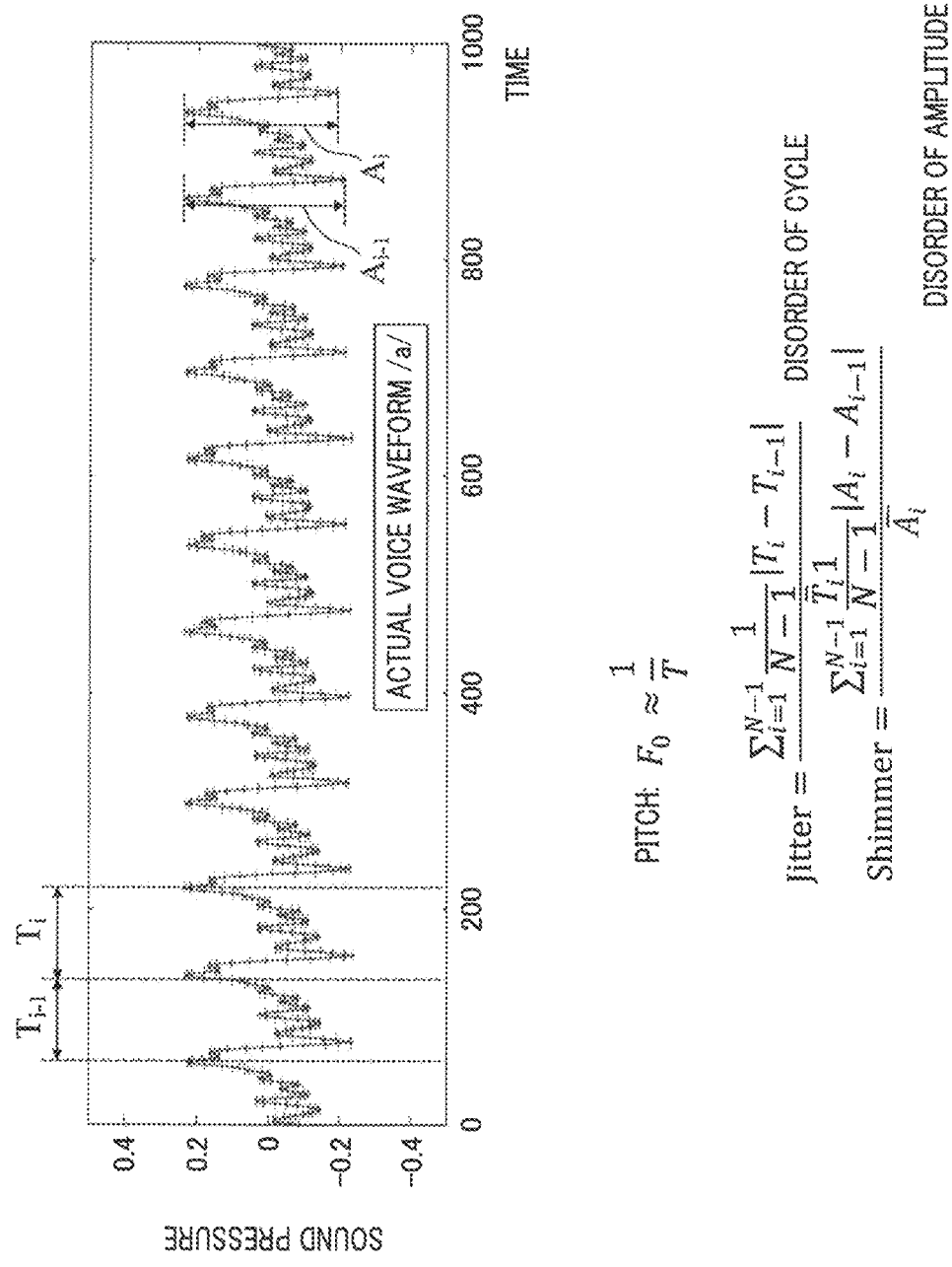
FIG. 4 is a diagram for explaining the second acoustic parameter.

FIG. 4 is an explanatory diagram associated with wave information regarding a waveform. A horizontal axis represents a time t and a vertical axis represents a sound pressure.

The wave information regarding a waveform includes a jitter (Jitter) and a shimmer (Shimmer). The jitter (Jitter) indicates the disorder of a cycle on a time axis when a time per cycle is Ti and can be explained using the following expression.

$$\text{Jitter} = \frac{\sum_{i=1}^{N-1} \frac{1}{N-1} |T_i - T_{i-1}|}{T_i} \quad \text{Disorder of cycle} \quad \text{[Math. 3]}$$

The shimmer (Shimmer) indicates the disorder of an amplitude with respect to a sound pressure when a sound pressure per amplitude is Ai and can be explained using the following expression.

$$\text{Shimmer} = \frac{\sum_{i=1}^{N-1} \frac{1}{N-1} |A_i - A_{i-1}|}{\overline{A_i}} \quad \text{Disorder of amplitude} \quad \text{[Math. 4]}$$

(3. Zero-Point Crossing Rate)

Figure 5:
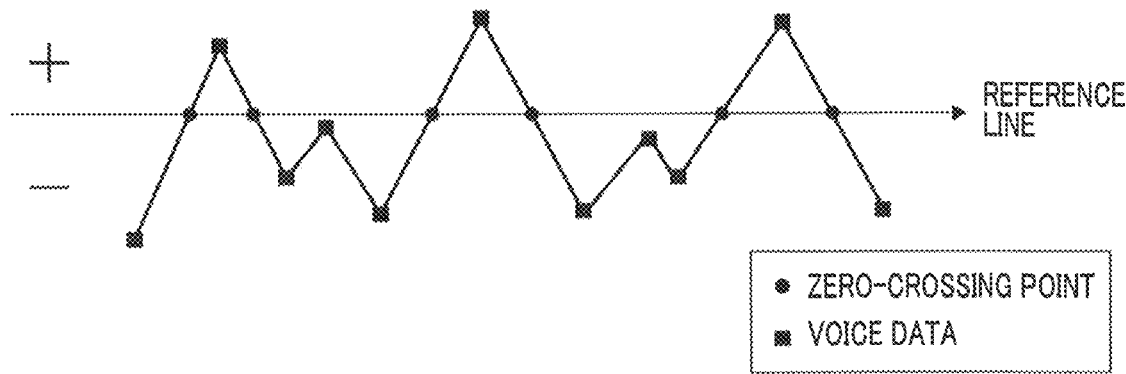
FIG. 5 is a diagram for explaining the second acoustic parameter.

FIG. 5 is an explanatory diagram associated with a zero-point crossing rate. The zero-point crossing rate is obtained by calculating the number of times per unit time in which a waveform of a sound pressure of a voice crosses a reference pressure, as a degree of severity of a change in waveform in the voice. The zero-point crossing rate will be described in detail later.

(4. Hurst Index)

Figure 6:
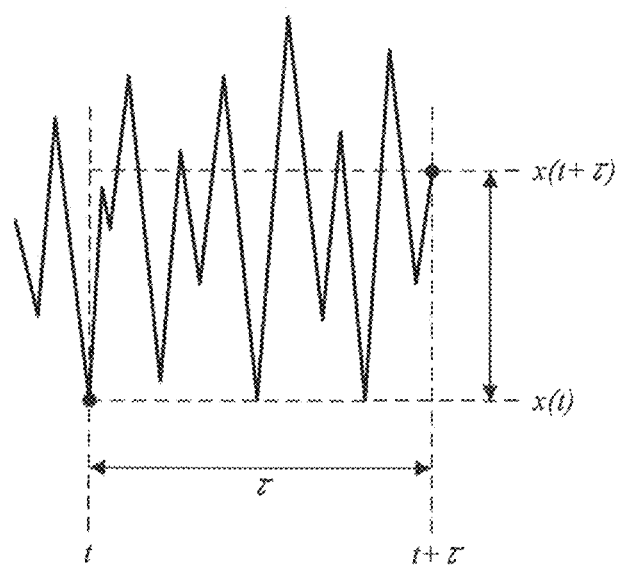
FIG. 6 is a diagram for explaining the second acoustic parameter.

FIG. 6 is an explanatory diagram associated with a Hurst index. The Hurst index indicates the correlation of a change in waveform of a voice. The Hurst index will be described in detail later.

(5. Voice Onset Time (VOT))

Figure 7:
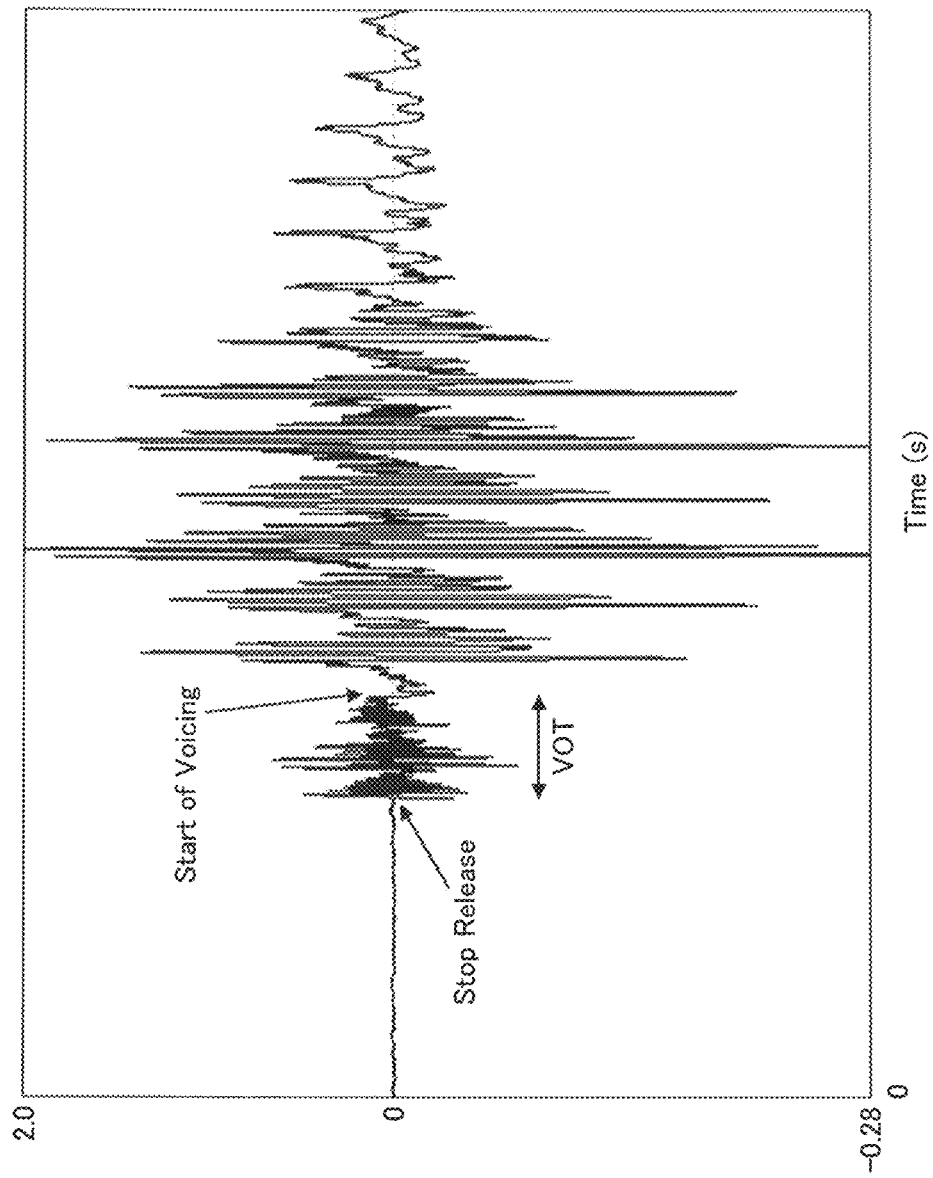
FIG. 7 is a diagram for explaining the second acoustic parameter.

FIG. 7 is an explanatory diagram associated with a voice onset time (VOT). The VOT means a time from when air begins to flow (Start of Voicing) to vocal cords begin to vibrate (Stop Release), that is, a voice onset time (VOT). In FIG. 7, a horizontal axis represents a time t and a vertical axis represents a sound pressure.

(6. to 11. Various Statistics in Speech Data)

Figure 8:
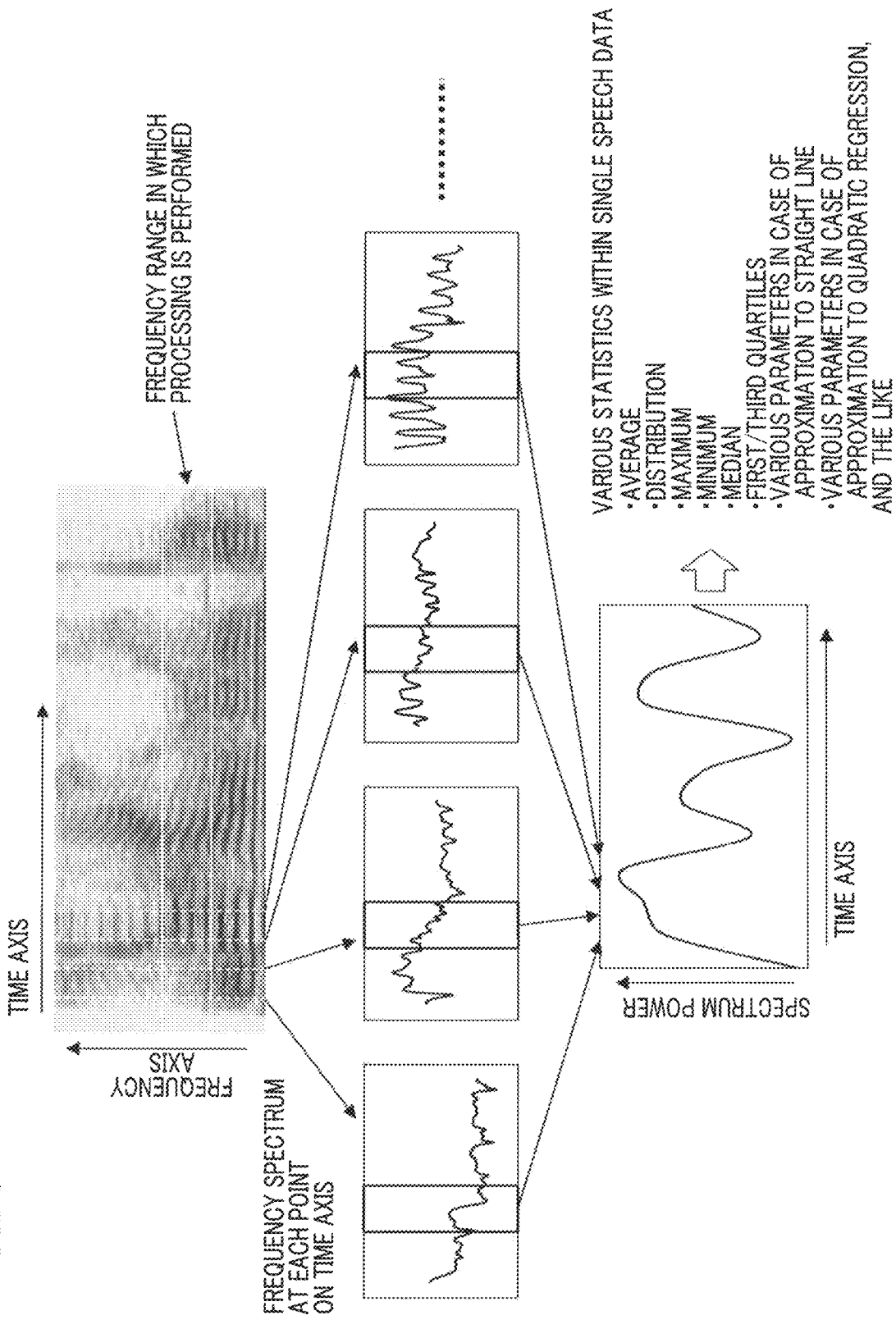
FIG. 8 is a diagram for explaining the second acoustic parameter.

FIG. 8 includes various explanatory diagrams associated with statistics in speech data. The upper part shows a graph of an intensity of a voice of a frequency component in which a horizontal axis represents a time t and a vertical axis represents a frequency axis. In the graph of the upper part, a level of an intensity of a voice is indicated by shades of color.

In the upper part graph, a frequency domain to be processed is trimmed and a frequency spectrum at each point in the trimmed region is shown in the middle part.

The middle part graph shows a frequency spectrum at each point on the time axis of the upper part graph. Thus, a portion of the upper part shown in dark color indicates a high voice intensity and a portion thereof shown in light color indicates a low voice intensity. Furthermore, the lower part graph is obtained by performing spectrum-analysis on a frequency spectrum in the middle part and representing a vertical axis as a power spectral density and a horizontal axis as a time axis.

From the lower part graph, statistics of a distribution in speeches associated with a coefficient of a mel frequency cepstrum (a first quartile, a median, a third quartile, a 95% point, an arithmetic mean, a geometric mean, a difference between a third quartile and a median, and the like), statistics of a distribution in speeches at a rate of change of a frequency spectrum (a first quartile, a median, a third quartile, a 95% point, an arithmetic mean, a geometric mean, a difference between a third quartile and a median, and the like), statistics of a distribution in speeches associated with a time change of a coefficient of a mel frequency cepstrum (a first quartile, a median, a third quartile, a 95% point, an arithmetic mean, a geometric mean, a difference between a third quartile and a median, and the like), statistics of a distribution in speeches of a time change of a coefficient of a mel frequency cepstrum which is associated with the time change (a first quartile, a median, a third quartile, a 95% point, an arithmetic mean, a geometric mean, a difference between a third quartile and a median, and the like), a square error for a frequency spectrum 90% roll-off with respect to quadratic regression approximation on a time change in speech, and an arithmetic error of a frequency spectrum center of gravity with respect to quadratic regression approximation on a time change in speech are calculated.

Subsequently, in Step S106 of FIG. 10, the subject is subjected to scoring after a feature quantity has been set. The scoring is processing of calculating a score of the subject on the basis of a disease-specific feature quantity F(a) and the first acoustic parameter. The score of the subject acquired through the scoring is transmitted to the detection unit 112 and the estimation unit 113.

(Detection Unit 112)

Subsequently, in Step S107, the detection unit 112 determines whether a health reference range created on the basis of the feature quantity is set. The health reference range is a region in which a healthy subject and an individual subject with a disease are distinguished from a regression straight line created using the feature quantity F(a).

The process of the detection unit 112 proceeds to the process of Step S109 when it is determined in Step S107 that the health reference range is set. When it is determined that the health reference range is not set, in Step S108, the health reference range is set on the basis of the feature quantity. Information regarding a reference range is transmitted to the estimation unit 113.

Subsequently, in Step S109, the detection unit 112 detects a disease which exceeds the health reference range from the score of the subject calculated using the calculation unit 111.

Subsequently, in Step S110, the detection unit 112 determines whether a plurality of detected disease are present. When it is determined that a detected disease is not present or when it is determined that one detected disease is present, the process proceeds to the process of Step S112.

When it is determined that a plurality of diseases detected in Step S110 are present, in Step S111, the feature quantity is improved by comparing common items and coefficients of the amounts of feature of the detected diseases. The result of improving the feature quantity may be output to the recording device 120 configured to record the estimation program or the database (DB) server B for machine learning. The improvement of the feature quantity may be compared and verified until a significant difference occurs in the plurality of amounts of feature. When common items are present between the detected amounts of feature of the diseases, first, differences in the common items may be compared, and then individual amounts of feature may be compared.

Also, as a method for comparison, in addition to comparison through multiplication, comparison through range calculation may be performed. For example, the amount of disease-specific feature may be improved by comparing amounts of disease-specific feature and selecting maximum values or adding the maximum values.

Also, when sufficient differences are confirmed between the plurality of detected diseases and the health reference range, the plurality of diseases may be detected as final candidates. Furthermore, a user may manually adjust the improvement of the feature quantity.

After the feature quantity has been improved, the score of the subject acquired in Step S106 is calculated again if necessary. The improved feature quantity and the score result which has been calculated again are transmitted to the estimation unit 113. After all of the processing in the detection unit 112 is completed, the process proceeds to the process of Step S112.

(Estimation Unit 113)

Subsequently, in Step S112, the estimation unit 113 estimates a disease from the feature quantity acquired using the calculation unit 111 and the detection unit 112 and the score of the subject based on the acquired feature quantity.

Figure 9:
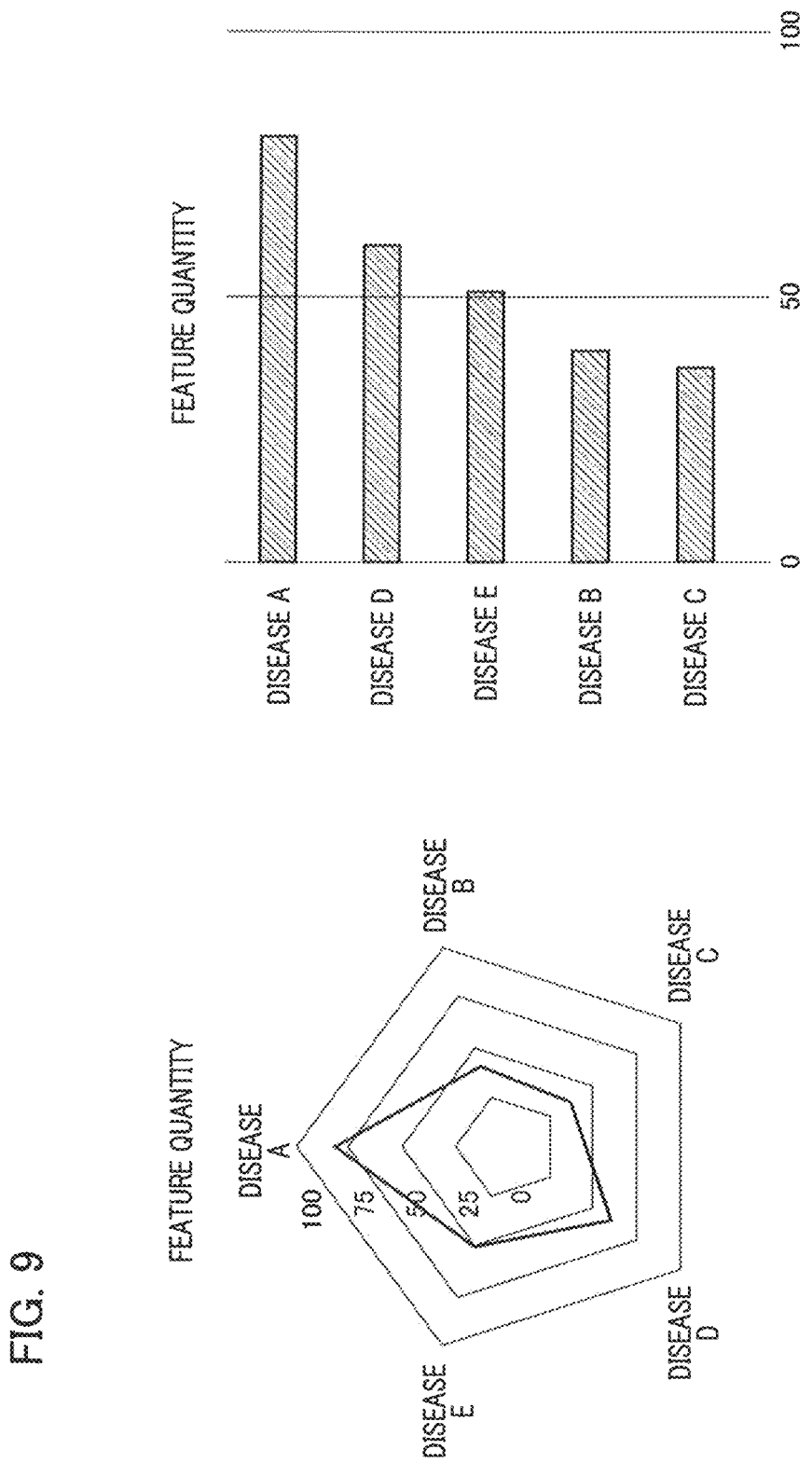
FIG. 9 is a diagram illustrating an example of scoring.

Subsequently, in Step S113, the estimation unit 113 outputs the estimation result to the communication terminal 200. As a method for estimating a disease, the disease may be estimated by selecting a disease having the largest value among differences between the score of the subject and the health reference range. Furthermore, when a sufficient difference is confirmed between the plurality of detected diseases, as illustrated in FIG. 9, scores for the plurality of diseases may be shown and a final determination may be performed by a user.

The estimation unit 113 may estimate a degree of health of the subject in accordance with a distance between the score of the subject calculated in Step S106 and a boundary line of the reference range set in Step S108. Furthermore, the estimation unit 113 may output information indicating the estimated health state and degree of health of the subject to the communication terminal 200.

Finally, the estimation apparatus 100 ends the estimation processing. The estimation apparatus 100 repeatedly performs the process of Steps S101 to S113 each time the estimation apparatus 100 receives voice data of the subject from the communication terminal 200.

When information regarding the reference range is determined in advance using the estimation apparatus 100 or an external computer apparatus in the process illustrated in FIG. 10 and is recorded in the recording device 120 of the estimation apparatus 100, the process of Steps S104, S105, S107, and S108 may be omitted.

As described above, in a first embodiment, the calculation unit 111 calculates the score of the subject on the basis of the feature quantity using voice data of the subject acquired from the communication terminal 200. The estimation unit 113 estimates a health state or a disease of the subject on the basis of the comparison between the calculated score of the subject and the reference range set using the detection unit 112.

Figure 13A:
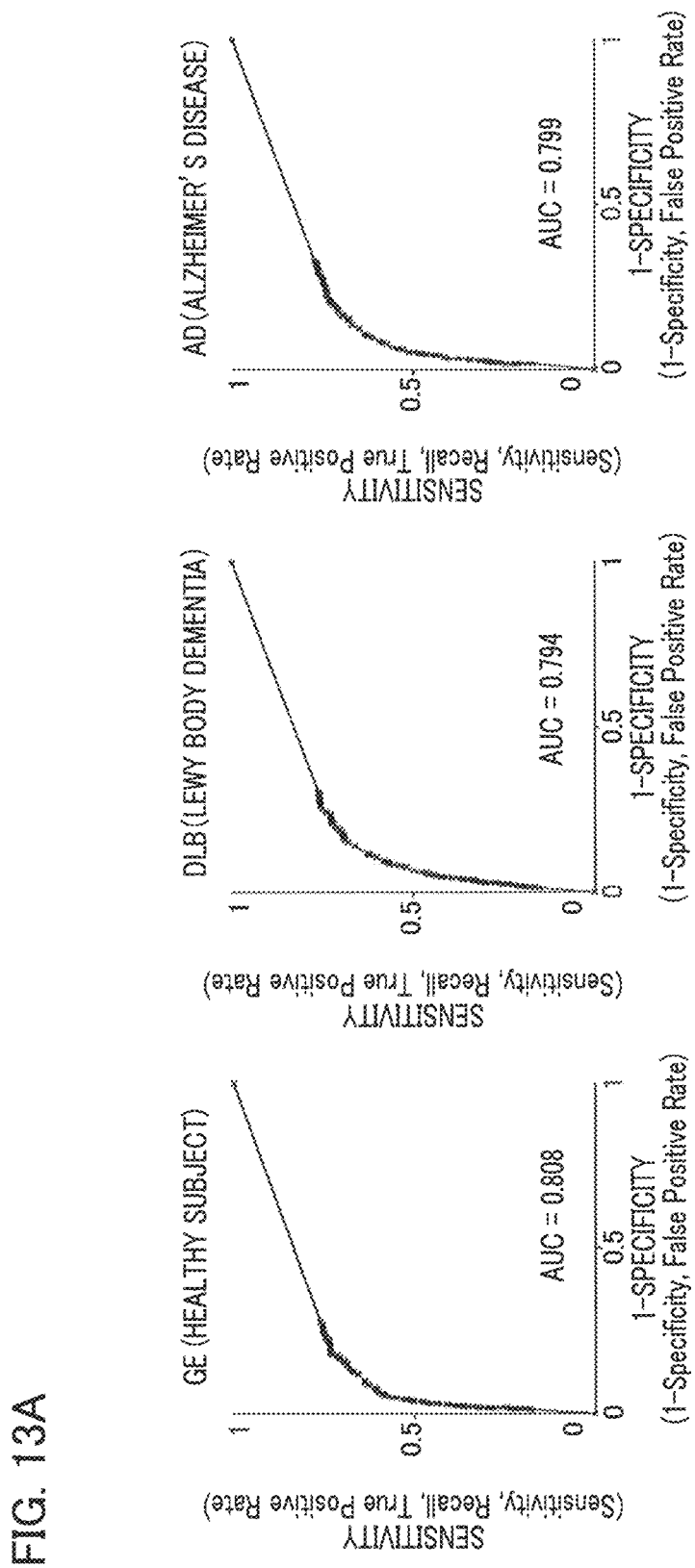
FIG. 13A is an ROC curve illustrating the precision of estimation of the present invention.
Figure 13B:
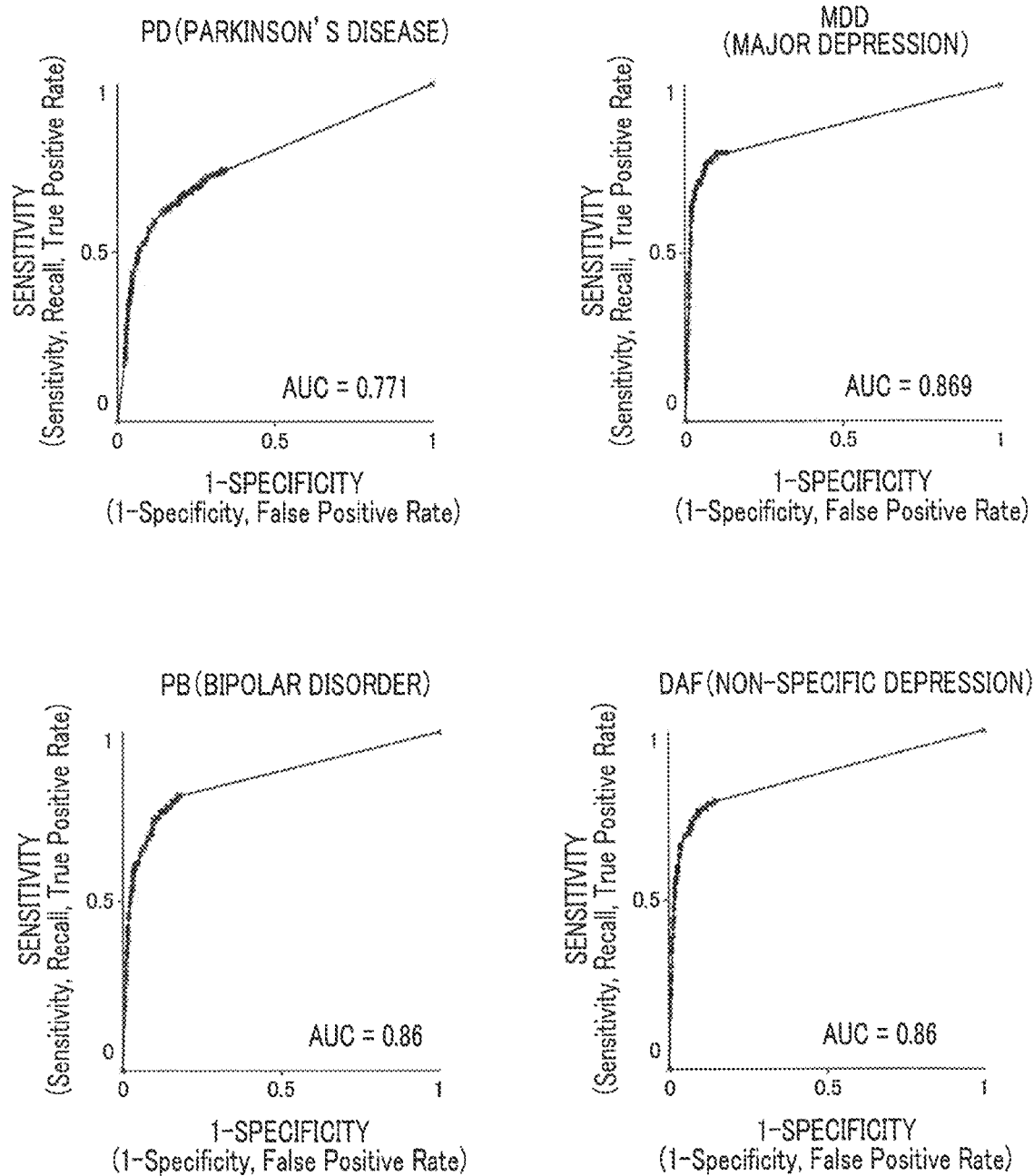
FIG. 13B is an ROC curve illustrating the precision of estimation of the present invention.

FIG. 13 illustrates an example of the result estimated through Steps S101 to S113 described above. FIG. 13 is a graph of an ROC curve illustrating a healthy subject or a specific disease and other separation performances. A horizontal axis represents specificity and a vertical axis represents sensitivity. In other words, the horizontal axis represents false positive rates and the vertical axis represents true positive rates. The ROC curves in FIG. 13 illustrate the true positive rates having high values when all of the false positive rates are low.

Also, all areas under an ROC curve (AUCs) are higher than 0.5 and a significant difference is confirmed between this case and a case in which identification is performed randomly. Diseases for which separation performances have been verified include Lewy body dementia, an Alzheimer's disease, a Parkinson's disease, major depression, a bipolar disorder, and non-specific depression. The AUCs on the ROC curves are 0.794 for Lewy body dementia, 0.799 for an Alzheimer's disease, 0.771 for a Parkinson's disease, 0.869 for major depression, 0.86 for a bipolar disorder, and 0.86 for non-specific depression. Diseases which can be estimated using the present invention are not limited to the diseases described above.

As described above, when the process of Steps S101 to S113 illustrated in FIG. 10 is performed, the estimation apparatus 100 can estimate a specific disease from a plurality of mental/neurological diseases with high precision in an advanced and professional manner.

Second Embodiment

An embodiment in a case in which a zero-point crossing rate and a Hurst index are selected will be described in detail below as a second acoustic parameter.

The calculation unit 111 calculates a zero-point crossing rate as a degree of severity of a change in waveform in a voice. Furthermore, the calculation unit 111 calculates a Hurst index indicating the correlation of the change in waveform of the voice. The calculation unit 111 outputs the calculated zero-point crossing rate and Hurst index of the subject to the detection unit 112 and the estimation unit 113.

Since the estimation unit 113 estimates the health state of the subject from the zero-point crossing rate and the Hurst index of the subject calculated by the calculation unit 111, the detection unit 112 sets a health reference range indicating a healthy state in which a person is not suffering from a disease such as depression.

For example, the calculation unit 111 reads out voice data of a plurality of people whose health state regarding a determination concerning whether they are suffering from diseases such as depression is known from the database or the recording device 120 of the estimation apparatus 100 and calculates a second acoustic parameter including a zero-point crossing rate and a Hurst index of each of a plurality of people from the read-out voice data.

Also, the calculation unit 111 performs linear classification processing such as a linear discrimination expression and logistic regression analysis on a distribution of the zero-point crossing rate and the Hurst index of a plurality of people calculated by the calculation unit 111 in a two-dimensional space of the zero-point crossing rate and the Hurst index and creates a feature quantity on the basis of these linear models.

Subsequently, the detection unit 112 sets a boundary line used for separating a region of a person suffering from depression or the like and a reference range of a healthy person not suffering from depression or the like on the basis of the feature quantity created using the calculation unit 111. The detection unit 112 outputs information indicating a reference range including the determined boundary line to the estimation unit 113.

When the feature quantity has been created, there is no need to distinguish between diseases, and information indicating the health reference range is set in advance using the estimation apparatus 100 or an external computer apparatus and recorded in the recording device 120 of the estimation apparatus 100, the detection unit 112 may be omitted.

The estimation unit 113 estimates a health state of the subject (for example, a determination concerning whether the subject is in a depression state or the like) on the basis of the score of the zero-point crossing rate and the Hurst index of the subject calculated by the calculation unit 111 and the reference range set using the detection unit 112. Furthermore, the estimation unit 113 outputs information indicating the estimated health state to the communication terminal 200.

FIG. 14 illustrates an example of voice data acquired via the communication terminal 200 illustrated in FIG. 1. FIG. 14 illustrates a time change of a sound pressure of a voice of speech of the subject acquired via the communication terminal 200. A horizontal axis of FIG. 14 represents a time t and a vertical axis represents a sound pressure.

FIG. 14 illustrates data of a speech unit having the speech of "ARIGATOU" among the voice data of the speech by the subject. Times t0, t1, t2, t3, and t4 indicate start times at which the speech of the words "A," "RI," "GA," "TO," and "U" included in the speech unit is performed. Although calculation processing of the calculation unit 111 performed on the voice data in which the word "RI" of the speech unit, i.e., the speech of "ARIGATOU," will be described, the calculation unit 111 also performs the same or similar calculation processing on words other than "ARIGATOU" and other speech units.

The calculation unit 111 calculates the zero-point crossing rate and the Hurst index using the voice data acquired from the communication terminal 200 for each window WD of the number of samples such as 512. As illustrated in FIG. 14, since the sound pressure changes significantly in the speech of each word, for example, the calculation unit 111 calculates an average value of the sound pressure for each window WD1 of the number of samples such as 30 smaller than that of the window WD to calculate the zero-point crossing rate and uses the average value calculated using each window WD1 as a reference pressure of each window WD1. The calculation unit 111 measures the number of times the sound pressure of the subject crosses the calculated reference pressure (average value) in each window WD1 and calculates the zero-point crossing rate.

The calculation unit 111 calculates the average value of the zero-point crossing rates calculated using each window WD1 as a zero-point crossing rate ZCR of the window WD.

On the other hand, a standard deviation $\sigma(\tau)$ of a difference between a sound pressure $x(t)$ at a time t and a sound pressure $x(t+\tau)$ at a time away from the time t by a time $\tau$ is associated as illustrated in Expression (1). Furthermore, it is known that there is a power-based relationship between the time interval $\tau$ and the standard deviation $\sigma(\tau)$ as illustrated in Expression (2). In addition, H in Expression (2) is a Hurst index.

[Math. 5]

$$\sigma(\tau) = \sqrt{\langle (x(t+\tau)-x(t)-\langle x(t+\tau)-x(t)\rangle)^2 \rangle} \quad (1)$$

$$\sigma(\tau) \propto \tau^H \quad (2)$$

For example, in the case of voice data such as white noise, the Hurst index H is "0" because there is no temporal correlation between data of the voice data. Furthermore, the Hurst index H has a value larger than "0" as the voice data changes from white noise to pink noise or Brownian noise, that is, a waveform of a voice has a temporal correlation.

For example, when the voice data is Brownian noise, the Hurst index H is 0.5. Furthermore, the Hurst index H has a value between 0.5 and 1 as the voice data has a correlation stronger than that of the Brownian noise, that is, a degree in which the voice data depends on a state thereof in the past increases.

For example, the calculation unit 111 obtains the standard deviation σ(τ) of the voice data for each τ whose time interval τ is between 1 to 15 in the window WD and calculates the Hurst index H by performing regression analysis on the obtained standard deviation σ(τ) of each time interval τ.

The calculation unit 111 moves the window WD at a predetermined interval such as a quarter of a width of the window WD and calculates the zero-point crossing rate ZCR and the Hurst index H in each window WD. Furthermore, the calculation unit 111 averages the calculated zero-point crossing rates ZCR and Hurst indexes H of all windows WD and outputs, as a zero-point crossing rate and a Hurst index of a subject PA, the averaged zero-point crossing rate ZCR and Hurst index H to the estimation unit 113.

Figure 15:
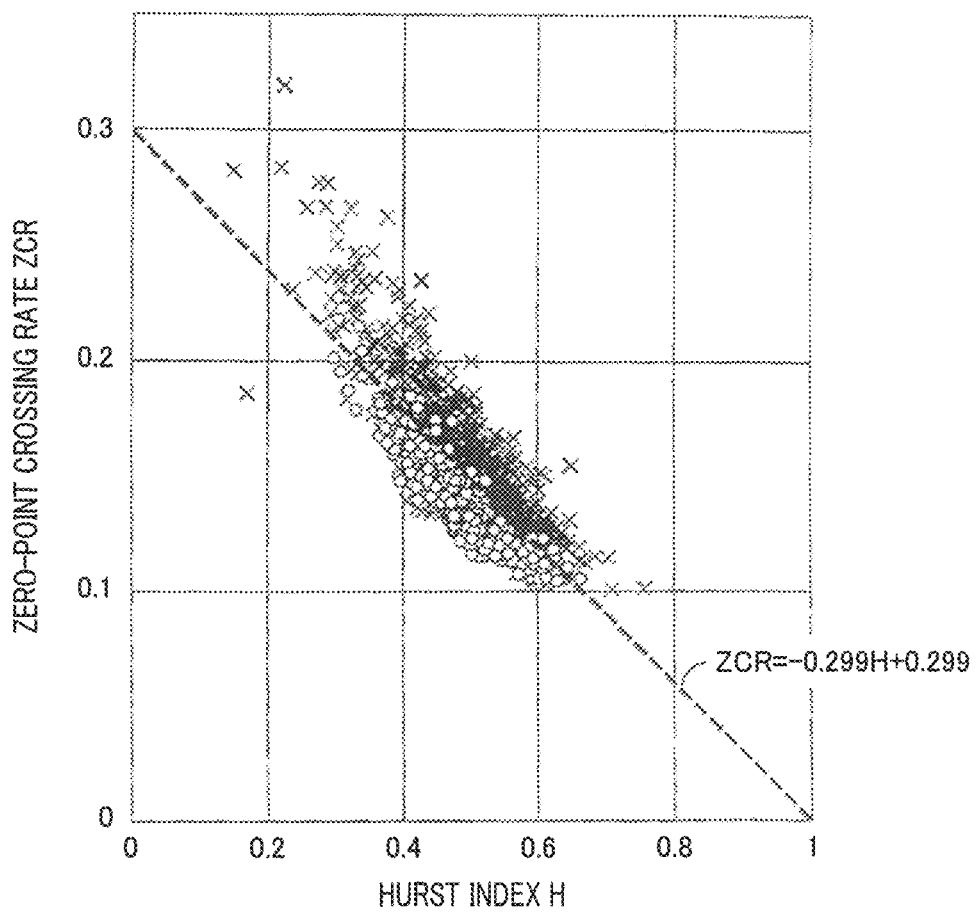
FIG. 15 is a diagram for describing regression analysis of the present invention.

FIG. 15 illustrates an example of a distribution of a zero-point crossing rate ZCR and a Hurst index H of a plurality of people calculated by the calculation unit 111 illustrated in FIG. 1. A vertical axis of FIG. 15 represents a zero-point crossing rate ZCR and a horizontal axis represents a Hurst index H.

Also, in FIG. 15, a zero-point crossing rate ZCR and a Hurst index H of a person suffering from a disease such as depression are indicated by a cross and a zero-point crossing rate ZCR and a Hurst index H of a healthy person are indicated by a circle. A distribution of the zero-point crossing rate ZCR and the Hurst index H illustrated in FIG. 15 is generated using voice data of 1218 people. Furthermore, 697 people of the total of 1218 people are suffering from a disease such as depression and 521 people are healthy people.

The calculation unit 111 performs linear classification processing such as a linear discrimination expression or logistic regression analysis on the distribution of the zero-point crossing rate ZCR and the Hurst index H of the plurality of people illustrated in FIG. 15. The detection unit 112 determines a boundary line indicated by a broken line used for separating a person suffering from a disease such as depression from a healthy person.

In the case of FIG. 15, the boundary line shown by the broken line is represented by ZCR=−0.299H+0.299. The detection unit 112 outputs information regarding a reference range including the determined boundary line to the estimation unit 113 using a region below the boundary line indicated by the broken line as the reference range and sets the reference range in the estimation unit 113.

Although the vertical axis of the zero-point crossing rate ZCR and the horizontal axis of the Hurst index H of FIG. 15 are linear axes, when the boundary line indicated by the broken line is represented by an exponential function, a power function, or the like, it is preferable to use logarithmic axes as the axes to show the boundary line as a straight line.

Figure 16:
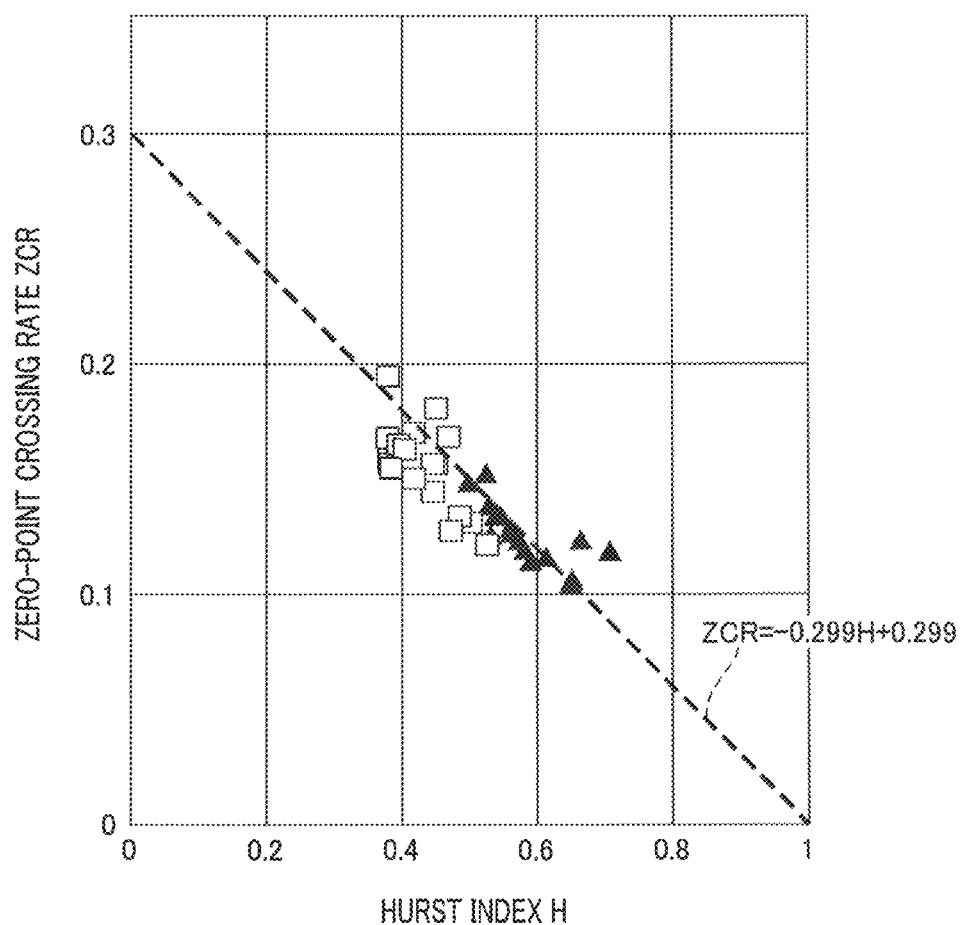
FIG. 16 is a diagram for describing regression analysis of the present invention.

FIG. 16 illustrates an example of a distribution of a zero-point crossing rate ZCR and a Hurst index H according to a voice data acquisition environment. As in FIG. 15, a vertical axis of FIG. 16 represents the zero-point crossing rate ZCR and a horizontal axis represents the Hurst index H. Furthermore, in FIG. 16, a boundary line determined by the detection unit 112 from the distribution of the zero-point crossing rate ZCR and the Hurst index H illustrated in FIG. 15 is indicated by a broken line.

FIG. 16 illustrates, for example, a distribution of a zero-point crossing rate ZCR and a Hurst index H calculated using voice data obtained by sampling, by the communication terminal 200, a voice of the subject at a sampling frequency of 11 kHz using black triangles.

On the other hand, for example, the communication terminal 200 down-samples voice data of the subject PA obtained by performing sampling at 11 kHz at a sampling frequency of 8 kHz to transmit the voice data to the estimation apparatus 100 over the network NW. FIG. 16 illustrates a distribution of the zero-point crossing rate ZCR and the Hurst index H calculated using the voice data down-sampled at 8 kHz using white rectangles.

As illustrated in FIG. 16, the zero-point crossing rate ZCR and the Hurst index H of the subject PA are affected by the deterioration of sound quality (an increase in noise) due to down-sampling. That is to say, the zero-point crossing rate ZCR of the down-sampled voice data has a value larger than that of the zero-point crossing rate ZCR of the voice data sampled at 11 kHz because noise increases and the number of times a sound pressure of a voice crosses a reference pressure increases.

On the other hand, the Hurst index H of the down-sampled voice has a value smaller than that of the Hurst index H of the voice data sampled at 11 kHz because the voice data approaches white noise due to an increase in noise.

However, although the zero-point crossing rate ZCR and the Hurst index H are affected by the down-sampling, the zero-point crossing rate ZCR and the Hurst index H do not change independently of each other and change to have a relationship. That is to say, as illustrated in FIG. 16, the zero-point crossing rate ZCR and the Hurst index H change along the boundary line shown by the broken line while having a mutual correlation with respect to the deterioration of sound quality due to down-sampling or the like.

For this reason, the deterioration of the sound quality due to down-sampling or the like does not affect an operation of the estimation unit 113 configured to determine whether the zero-point crossing rate ZCR and the Hurst index H of the subject are included within the reference range. That is to say, the zero-point crossing rate ZCR and the Hurst index H have robustness against the deterioration of the sound quality of the down-sampling or the like. Furthermore, the estimation apparatus 100 can estimate a health state of the subject with higher precision than in the related art, regardless of the voice data acquisition environment.

Figure 11:
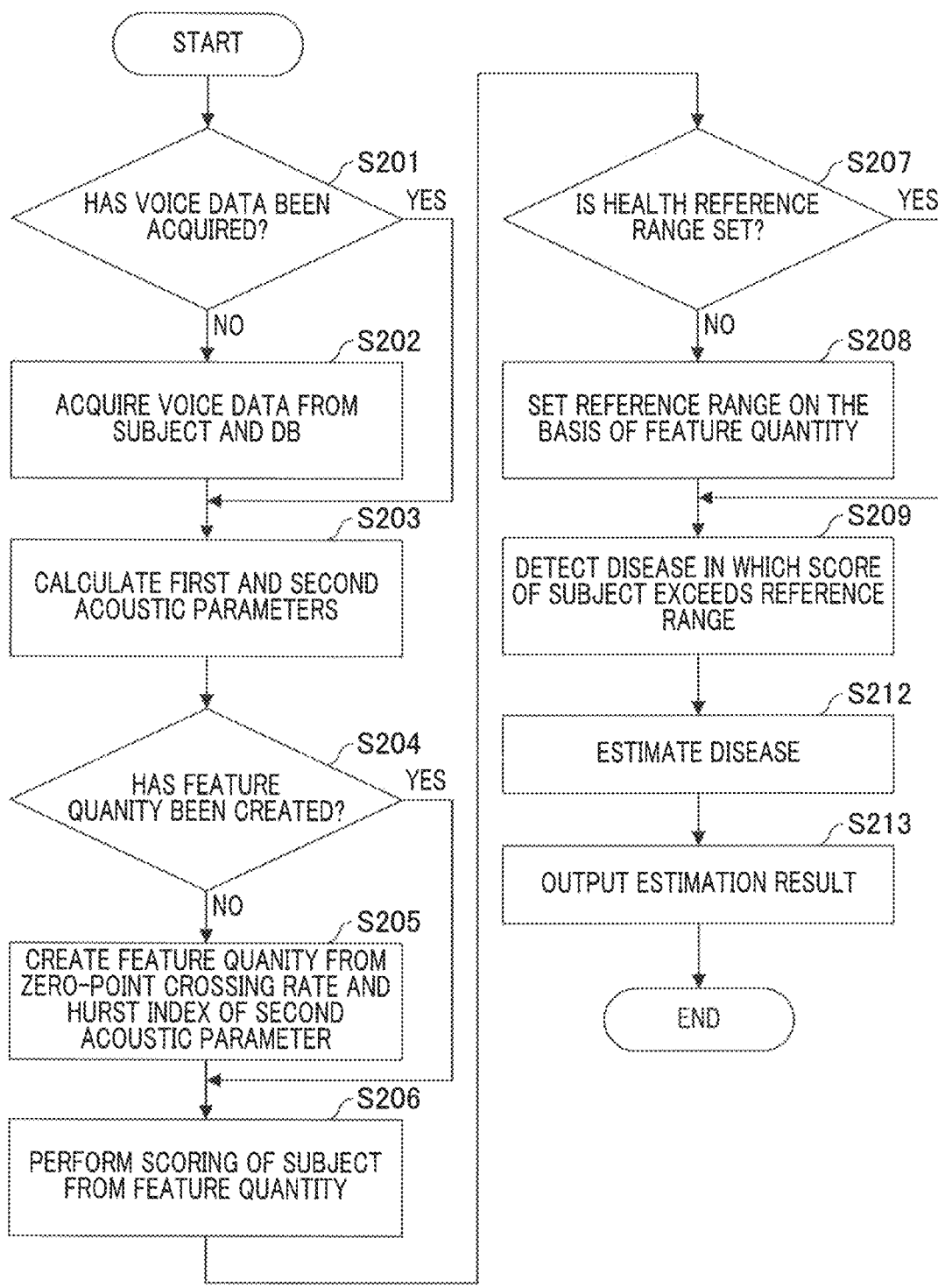
FIG. 11 is a flowchart for describing the present invention.

FIG. 11 illustrates an example of estimation processing in the estimation apparatus 100 illustrated in FIG. 1. The processing illustrated in FIG. 11 is realized using the computational processing device 110 of the estimation apparatus 100 configured to perform the estimation program recorded in the recording device 120 of the estimation apparatus 100.

If the process is started, in Step S201, the calculation unit 111 determines whether the voice data has been acquired. There are two types of data as the voice data and one thereof is first voice data acquired from a subject which is a target. The other thereof is second voice data acquired from the database (DB) server B or the like of FIG. 2. The second voice data is associated with major depression in advance in the case of a second embodiment. The second voice data may be recorded in advance in the recording device 120 of the estimation apparatus 100 together with the estimation program.

When it is determined that the voice data has already been acquired, the process proceeds to the process of Step S203. When it is determined that the voice data has not been acquired yet, in Step S202, the voice data is acquired via the communication terminal 200, the database (DB) server B, and the like.

Subsequently, in Step S203, the calculation unit 111 calculates a first acoustic parameter and a second acoustic parameter, that is, a zero-point crossing rate ZCR and a Hurst index H, from the two types of acquired voice data. The second acoustic parameter may be recorded in advance in the recording device 120 of the estimation apparatus 100 together with the estimation program.

Subsequently, in Step S204, the calculation unit 111 determines whether a disease-specific feature quantity has been created. When it is determined that the feature quantity has already been created, the process proceeds to the process of Step S206. When it is determined that the feature quantity has not been created yet, in Step S205, the feature quantity is created on the basis of the zero-point crossing rate ZCR and the Hurst index H associated with major depression. To be specific, linear classification processing such as a linear discrimination expression and logistic regression analysis is performed on the distribution of the zero-point crossing rate ZCR and the Hurst index H.

Subsequently, in Step S206, scoring of the subject is performed. The scoring is processing of calculating a score of the subject on the basis of the disease-specific feature quantity and the first acoustic parameter. The score of the subject acquired through the scoring is transmitted to the detection unit 112 and the estimation unit 113.

Subsequently, in Step S207, the detection unit 112 determines whether the health reference range created on the basis of the feature quantity is set.

When it is determined in Step S207 that the health reference range is set, the process of the detection unit 112 proceeds to the process of Step S209. When it is determined that the health reference range is not set, in Step S208, the health reference range is set on the basis of the feature quantity.

Subsequently, in Step S209, the detection unit 112 detects whether the score associated with the zero-point crossing rate ZCR and the Hurst index H of the subject calculated by the calculation unit 111 is within the health reference range.

Subsequently, in Step S212, the estimation unit 113 estimates that the subject is suffering from a disease such as major depression when the score of the subject using the detection unit 112 exceeds the reference range. When the score of the subject associated with the zero-point crossing rate ZCR and the Hurst index H is located within the health reference range, the estimation unit 113 estimates that the subject is healthy. The estimation unit 113 outputs information indicating the estimated health state of the subject to the communication terminal 200.

For example, the estimation unit 113 may estimate a degree of health of the subject in accordance with a distance between the score of the subject associated with the zero-point crossing rate ZCR and the Hurst index H detected in Step S206 and the boundary line of the reference range set in Step S208. Furthermore, the estimation unit 113 may output information indicating the estimated health state and degree of health of the subject to the communication terminal 200.

Also, the estimation apparatus 100 ends the estimation processing. The estimation apparatus 100 repeatedly performs the process of Steps S201 to S213 each time the estimation apparatus 100 receives the voice data of the subject from the communication terminal 200.

In the process illustrated in FIG. 11, when the information regarding the reference range is determined in advance using the estimation apparatus 100 or an external computer apparatus and recorded in the recording device 120 of the estimation apparatus 100, the process of Steps S204, S205, S207, and S208 may be omitted.

As described above, in the second embodiment, the calculation unit 111 calculates the score of the feature quantity of the subject associated with the zero-point crossing rate ZCR and the Hurst index H using the voice data of the subject acquired from the communication terminal 200. The estimation unit 113 estimates a health state of the subject on the basis of the comparison between the calculated position of the zero-point crossing rate ZCR and the Hurst index H of the subject and the reference range set using the detection unit 112.

Also, although the zero-point crossing rate ZCR and the Hurst index H are affected by the deterioration of sound quality due to down-sampling or the like as illustrated in FIG. 16, the zero-point crossing rate ZCR and the Hurst index H do not change independently of each other and change to have a relationship. For this reason, the deterioration of sound quality due to down-sampling or the like does not affect an operation of the estimation unit 113 configured to determine whether the score of the subject associated with the zero-point crossing rate ZCR and the Hurst index H is included within the reference range. That is to say, the estimation apparatus 100 can estimate a health state of the subject with higher precision than in the related art, regardless of the voice data acquisition environment.

Also, the estimation apparatus 100 can obtain the zero-point crossing rate ZCR and the Hurst index H from the voice data of a subject suffering from major depression or the like, the voice data or the like including a long vowel or the like, or the like. For this reason, the estimation apparatus 100 can estimate a health state of the subject with higher precision than in the related art in which information indicating the correspondence between a voice parameter and an emotional state is used.

Third Embodiment

In the estimation apparatus 100 illustrated in FIG. 1, the calculation unit 111 can create a feature quantity on the basis of the relationship between the zero-point crossing rate ZCR and the Hurst index H which change in accordance with a ratio of noise included in the voice, for example, using a waveform model of the voice represented by Expression (3) and set a boundary line of a reference range.

[Math. 6]

$$x(t+1) = \alpha \times x(t) + \text{scale} \times \text{rand1} \times \text{SIGN}(\text{rand2}, \beta) \times \text{SIGN}((x(t) - x(t-1)), 0, 0) \quad (3)$$

Here, $x(t-1)$, $x(t)$, and $x(t+1)$ indicate voice data sampled at times $t-1$, $t$, and $t+1$. $\alpha$ indicates a degree in which voice data $x(t)$ depends on a state thereof in the past. For example, when $\alpha$ is 0, the voice data $x(t)$ is an independent value which does not depend on the state thereof in the past and indicates that the voice data $x(t)$ is white noise.

rand1 and rand2 represent uniform random numbers between 0 and 1. scale adjusts an amount of variation in which a waveform of the voice data x(t) varies in accordance with the uniform random number of rand1 and is set to, for example, a value such as 0.1 or 0.2. SIGN is a function represented by Expression (4) and determines the variation of the voice data x(t).

[Math. 7]

$$\mathrm{SIGN}(p, q) = \begin{cases} 1.0 & p < q \\ 0.0 & p = q \\ -1.0 & p < q \end{cases} \quad (4)$$

The voice data x(t) maintains an increasing or decreasing state in the case of p>q and changes a state thereof from an increasing state to a decreasing state or from a decreasing state to an increasing state in the cased of p<q. Furthermore, the voice data x(t) maintains the same state as in at present and does not change in the case of p=q. β adjusts the variation of the voice data x(t) in accordance with the uniform random number of rand2 via the function SIGN. For example, when α is set to 1 and β is set to 0.5, the voice data x(t) can reproduce a waveform similar to that of Brownian noise. The waveform model of the voice represented by Expression (3) is an example and may be represented using another function.

For example, the calculation unit 111 changes β between 0 and 1 using the waveform model of the voice of Expression (3) in which α is set to 1 and calculates the zero-point crossing rate ZCR and the Hurst index H from the voice data x(t) at each β value. Furthermore, the calculation unit 111 performs regression analysis processing such as a least squares method on the distribution of the zero-point crossing rate ZCR and the Hurst index H at each calculated β value. The calculation unit 111 determines, as a boundary line, a straight line passing through the zero-point crossing rate ZCR and the Hurst index H of each β value. In the case of the waveform model of the voice represented by Expression (3), the boundary line determined using the calculation unit 111 is represented by ZCR=−0.299H+0.305 and is a straight line similar to the boundary line of FIG. 15 indicated by a wavy line. Thus, the estimation apparatus 100 can easily set the boundary line of the reference range without acquiring the voice data of a plurality of people to determine the boundary line of the reference range.

Also, the calculation unit 111 outputs information regarding the reference range including the determined boundary line to the estimation unit 113 and sets the reference range to the estimation unit 113.

When the information regarding the reference range is determined in advance using the estimation apparatus 100 or an external computer apparatus and recorded in the recording device 120 of the estimation apparatus 100, the calculation unit 111 may be omitted.

Figure 12:
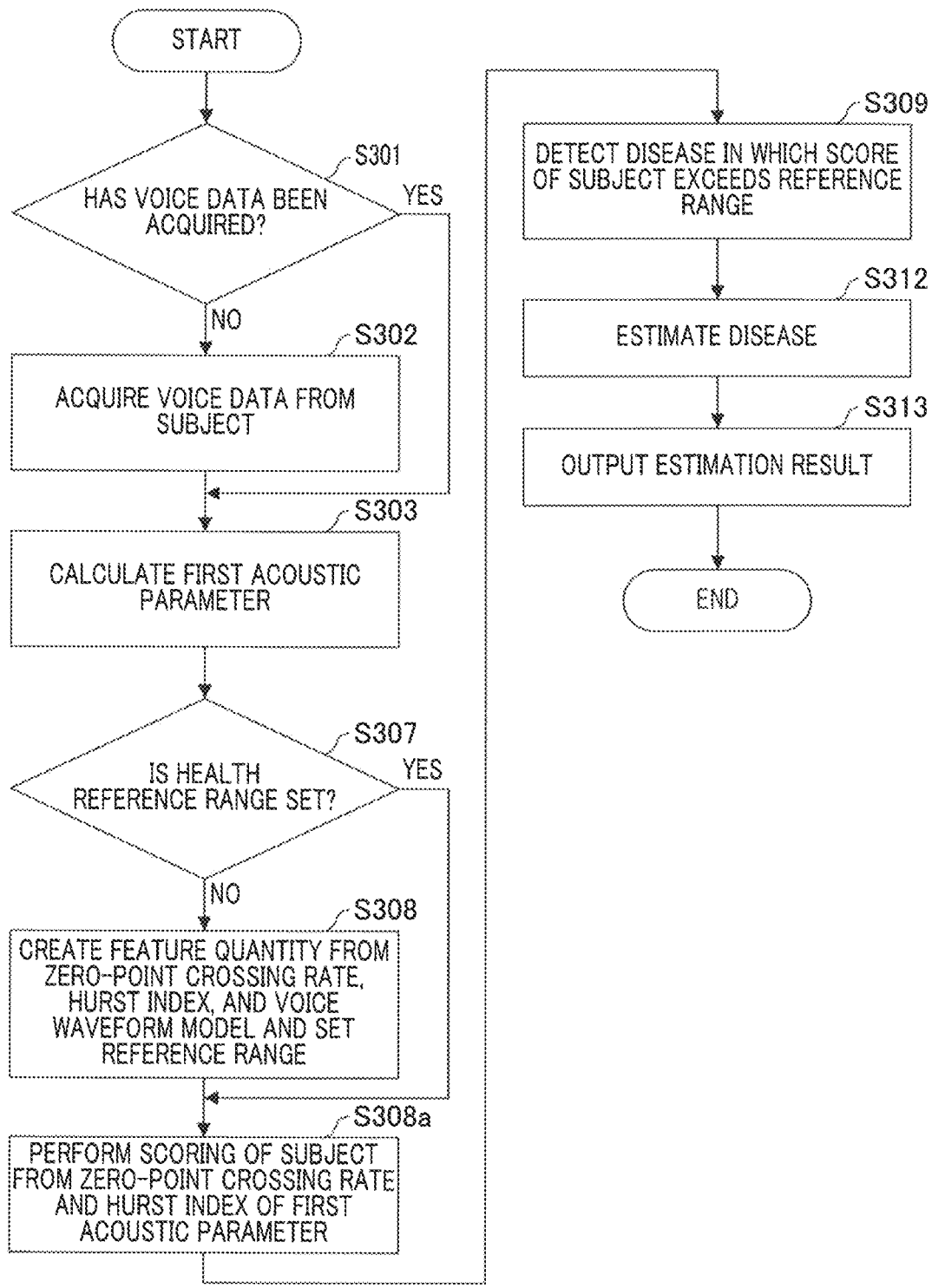
FIG. 12 is a flowchart for describing the present invention.

FIG. 12 illustrates an example of the estimation processing in the estimation apparatus 100 illustrated in FIG. 1.

The processing illustrated in FIG. 12 is implemented using the computational processing device 110 of the estimation apparatus 100 configured to execute the estimation program recorded in the recording device 120 of the estimation apparatus 100. That is to say, the process illustrated in FIG. 12 illustrates another embodiment of the estimation method and the estimation program.

If the process is started, in Step S301, the calculation unit 111 determines whether the voice data has been acquired. Furthermore, when it is determined that the voice data has been acquired, the process proceeds to the process of Step S303. When it is determined that the voice data has not been acquired yet, in Step S302, the voice data is acquired via the communication terminal 200 or the like.

Subsequently, in Step S303, the calculation unit 111 calculates the first acoustic parameter, that is, the zero-point crossing rate ZCR and the Hurst index H, from the acquired voice data.

Subsequently, in Step S307, the calculation unit 111 determines whether the health reference range is set. When it is determined that the health reference range is set, the process of the calculation unit 111 proceeds to the process of Step S308a. When the reference range is not set, the process of the calculation unit 111 proceeds to the process of Step S308.

In Step S308, the calculation unit 111 changes β between 0 to 1 using the waveform model of the voice of Expression (3) in which α is set to 1 and calculates the zero-point crossing rate ZCR and the Hurst index H from the voice data x(t) at each β value. Furthermore, the detection unit 112 performs regression analysis processing such as a least squares method on the distribution the zero-point crossing rate ZCR and the Hurst index H at each calculated β value and sets, as a boundary line, a straight line passing through the zero-point crossing rate ZCR and the Hurst index H at each β value.

Subsequently, in Step S308a, the detection unit 112 outputs information regarding the reference range including the boundary line set in Step S308 to the estimation unit 113 and sets the reference range.

Subsequently, in Step S308a, scoring of the subject is performed. The first acoustic parameter of the subject, that is, the zero-point crossing rate ZCR and the Hurst index H of the subject is used for the scoring in the third embodiment. The scoring result is output to the detection unit 112 and the estimation unit 113.

Subsequently, in Step S309, the detection unit 112 detects whether the zero-point crossing rate ZCR and the Hurst index H of the subject calculated in Step S308a are located within the reference range set in Step S308.

Subsequently, in Step S312, the estimation unit 113 estimates that the subject is suffering from major depression when the detection unit 112 determines that the score of the subject exceeds the reference range. When the score of the subject associated with the zero-point crossing rate ZCR and the Hurst index H is located with the health reference range, the estimation unit 113 estimates that the subject is healthy. The estimation unit 113 outputs information indicating the estimated health state of the subject to the communication terminal 200.

For example, the estimation unit 113 may estimate a degree of health of the subject in accordance with a distance between the score of the subject associated with the zero-point crossing rate ZCR and the Hurst index H calculated in Step S308a and the boundary line of the reference range set in Step S308. Furthermore, the estimation unit 113 may output information regarding the estimated health state and degree of health of the subject to the communication terminal 200.

Also, the estimation apparatus 100 ends the estimation processing. The estimation apparatus 100 repeatedly performs the process of Step S301 to Step S313 each time the estimation apparatus 100 receives the voice data of the subject from the communication terminal 200.

In the processing illustrated in FIG. 12, when the information regarding the reference range is determined in advance using the estimation apparatus 100 or an external computer apparatus and recorded in the recording device 120 of the estimation apparatus 100, the process of Steps S307 and S308 may be omitted.

As described above, in the third embodiment, the calculation unit 111 calculates the zero-point crossing rate ZCR and the Hurst index H of the subject using the voice data of the subject acquired via the communication terminal 200. The estimation unit 113 estimates a health state of a subject PA on the basis of the comparison between the calculated position of the zero-point crossing rate ZCR and the Hurst index H of the subject and the reference range set using the detection unit 112.

Also, although the zero-point crossing rate ZCR and the Hurst index H are affected by the deterioration of sound quality due to down-sampling or the like as illustrated in FIG. 16, the zero-point crossing rate ZCR and the Hurst index H do not change independently of each other and change to have the relationship. For this reason, deterioration of sound quality due to down-sampling or the like does not affect the operation of the estimation unit 113 configured to determine whether the zero-point crossing rate ZCR and the Hurst index H of the subject is included within the reference range. That is to say, the estimation apparatus 100 can estimate a health state of the subject with higher precision than in the related art, regardless of the voice data acquisition environment.

Also, the estimation apparatus 100 can obtain the zero-point crossing rate ZCR and the Hurst index H from the voice data of the subject suffering from major depression or the like, the voice data or the like including a long vowel, or the like. For this reason, the estimation apparatus 100 can estimate a health state of the subject with higher precision than in the related art in which information indicating the correspondence between a voice parameter and an emotional state is utilized.

The estimation apparatus may be applied to, for example, mobile terminal device applications, services, or search systems for robots, artificial intelligence, automobiles, call centers, the Internet, smartphones, tablet type terminals, or the like. Furthermore, the estimation apparatus may be applied to diagnostic devices, automatic inquiry devices, disaster triages, and the like.

Although the estimation apparatus has been mainly described above, the present invention may include a method for operating a medical apparatus configured to cause a medical apparatus which includes the estimation apparatus to be operated as described above or may be an estimation program for causing a computer to execute the same processing as in a medical apparatus, a non-temporary recording medium from which reading can be performed using a computer having the estimation program recorded therein, or the like.

The above detailed description may clarify the features and advantages of the embodiments. It is intended that the claims extend to the features and advantages of the embodiments as described above without departing from the gist thereof and the scope of rights. Furthermore, those skilled in the art need to be able to easily come up with any improvements or changes. Therefore, there is no intention to limit the scope of the embodiments having inventiveness to those described above and it is possible to rely on suitable improvements and equivalents included in the scope disclosed in the embodiments.

INDUSTRIAL APPLICABILITY

It is possible to provide a medical apparatus for estimating a mental/neurological disease with high precision.

REFERENCE SIGNS LIST

111 Calculation unit
112 Detection unit
113 Estimation unit
100 Estimation apparatus
200 Communication terminal

The invention claimed is:

1. An apparatus which estimates mental and neurological diseases from voice data of speech of a subject, comprising:
    a computational processing device;
    a recording device having an estimation program which causes the computational processing device to execute processing recorded therein;
    a calculation unit which creates a feature quantity from a second acoustic parameter associated with a disease in advance and calculates a score of the subject using the feature quantity and a first acoustic parameter and in which the first acoustic parameter is calculated from the voice data acquired from the subject;
    a detection unit which sets a reference range on the basis of the feature quantity and detects a disease whose score exceeds the reference range; and
    an estimation unit which estimates the mental and neurological diseases when the detection unit detects one or more diseases,
    wherein the apparatus estimates an Alzheimer's disease, Lewy body dementia, a Parkinson's disease, major depression, atypical depression, and a bipolar disorder, and the second acoustic parameter correlates with the mental and neurological diseases.

2. The apparatus according to claim 1, wherein the detection work is terminated when the number of diseases detected as exceeding the reference range is one or less, and the feature quantity is improved by comparing amounts of feature of the detected diseases when the number of diseases detected as exceeding the reference range is two or more.

3. A recording medium, comprising:
    an estimation program which causes the medical apparatus according to claim 1 to be executed recorded therein.

4. A method for operating a medical apparatus which estimates mental and neurological diseases from voice data of speech of a subject and in which the medical apparatus includes a computational processing device and a recording device having an estimation program which causes the computational processing device to execute processing recorded therein, comprising:
    creating, by a calculation unit of the computational processing device, a feature quantity from a second acoustic parameter associated with a disease in advance and calculating a score of the subject using the feature quantity and a first acoustic parameter, in which the first acoustic parameter is calculated from the voice data acquired from the subject;
    setting, by a detection unit of the computational processing device, a health reference range on the basis of the feature quantity and detecting a disease whose score exceeds the reference range; and
    estimating, by an estimation unit of the computational processing device, the mental and neurological diseases when the detection unit detects one or more diseases, wherein candidates for the mental and neurological diseases include an Alzheimer's disease, Lewy body dementia, a Parkinson's disease, major depression, atypical depression, and a bipolar disorder, and the second acoustic parameter correlates with the selected disease candidate.

5. The apparatus according to claim 1, wherein the detection work is terminated when the number of diseases detected as exceeding the reference range is one or less, and the feature quantity is improved by comparing amounts of feature of the detected diseases when the number of diseases detected as exceeding the reference range is two or more.

6. A recording medium, comprising:
an estimation program which causes the medical apparatus according to claim 2 to be executed recorded therein.

7. A recording medium, comprising:
an estimation program which causes the medical apparatus according to claim 5 to be executed recorded therein.

* * * * *